(12) United States Patent
Kurohara et al.

(10) Patent No.: US 10,751,228 B2
(45) Date of Patent: Aug. 25, 2020

(54) STRETCHABLE STRUCTURE FOR ABSORBENT ARTICLE AND DISPOSABLE DIAPER PANTS

(71) Applicant: Daio Paper Corporation, Ehime (JP)

(72) Inventors: Takeshi Kurohara, Ehime (JP); Masayo Obata, Ehime (JP); Sadanao Manabe, Tokyo (JP); Akifumi Hayashi, Tokyo (JP); Yosuke Mori, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 319 days.

(21) Appl. No.: 15/555,854

(22) PCT Filed: Mar. 25, 2016

(86) PCT No.: PCT/JP2016/059617
§ 371 (c)(1),
(2) Date: Sep. 5, 2017

(87) PCT Pub. No.: WO2016/158746
PCT Pub. Date: Oct. 6, 2016

(65) Prior Publication Data
US 2018/0042788 A1 Feb. 15, 2018

(30) Foreign Application Priority Data

Mar. 27, 2015 (JP) .................................. 2015-065634
Mar. 30, 2015 (JP) .................................. 2015-070285
(Continued)

(51) Int. Cl.
*A61F 13/49* (2006.01)
*A61F 13/513* (2006.01)
(Continued)

(52) U.S. Cl.
CPC ............ *A61F 13/513* (2013.01); *A61F 13/49* (2013.01); *A61F 13/496* (2013.01);
(Continued)

(58) Field of Classification Search
CPC .......... A61F 13/49011; A61F 13/49012; A61F 13/49019; A61F 13/4902; A61F 13/49061;
(Continued)

(56) References Cited

U.S. PATENT DOCUMENTS 7,217,261 B2 * 5/2007 Otsubo ............. A61F 13/49011
604/361
7,582,348 B2 * 9/2009 Ando ................... A61F 13/4902
428/103
(Continued)

FOREIGN PATENT DOCUMENTS

CN 101541284 A 9/2019
EP 2 186 495 5/2010
(Continued)

*Primary Examiner* — Catharine L Anderson
(74) *Attorney, Agent, or Firm* — Muncy, Geissler, Olds & Lowe, P.C.

(57) ABSTRACT

A stretchable structure of an absorbent article includes two sheet layers that extend in a stretchable direction and an orthogonal direction orthogonal to the stretchable direction; and elongated resilient and elastic members that are disposed between the sheet layers at predetermined intervals in the orthogonal direction and extend in the stretchable direction, wherein the two ends in the stretchable direction of each of the resilient and elastic members comprise fixed ends fixed to the two sheet layers, and the section between the fixed ends comprises a free section unfixed to the two sheet layers, at least one sheet bonding section is disposed in at least one inter-free region defined between the free sections adjacent to each other in the orthogonal direction, the two sheet layers being bonded in the at least one
(Continued)

inter-free region, and the two sheet layers in a contracted state conform with each other in a wave pattern in response to contraction of the resilient and elastic members.

19 Claims, 28 Drawing Sheets

(30) Foreign Application Priority Data

| Sep. 30, 2015 | (JP) | 2015-194542 |
|---|---|---|
| Sep. 30, 2015 | (JP) | 2015-194545 |
| Sep. 30, 2015 | (JP) | 2015-194549 |

(51) Int. Cl.
*A61F 13/496* (2006.01)
*A61F 13/15* (2006.01)
*A61F 13/42* (2006.01)

(52) U.S. Cl.
CPC .. *A61F 13/49011* (2013.01); *A61F 13/49019* (2013.01); *A61F 13/15203* (2013.01); *A61F 13/15577* (2013.01); *A61F 13/42* (2013.01); *A61F 2013/15406* (2013.01); *A61F 2013/15886* (2013.01); *A61F 2013/49053* (2013.01); *A61F 2013/51338* (2013.01)

(58) Field of Classification Search
CPC .. A61F 2013/49025; A61F 2013/49026; A61F 2013/49028; A61F 2013/49023; A61F 2013/49033; A61F 2013/49053
See application file for complete search history.

(56) References Cited

U.S. PATENT DOCUMENTS

| 7,758,558 | B2* | 7/2010 | Otsubo | A61F 13/49011 |
|---|---|---|---|---|
| | | | | 604/385.24 |
| 9,795,520 | B2* | 10/2017 | Kaneko | A61F 13/49011 |
| 2010/0076394 | A1* | 3/2010 | Hayase | A61F 13/15593 |
| | | | | 604/385.29 |
| 2011/0319853 | A1* | 12/2011 | Yamashita | A61F 13/49011 |
| | | | | 604/385.3 |

FOREIGN PATENT DOCUMENTS

| EP | 2 387 982 | | 11/2011 |
|---|---|---|---|
| EP | 2979670 | A1 | 2/2016 |
| JP | 2002-045399 | A | 2/2002 |
| JP | 2004-089403 | A | 3/2004 |
| JP | 2005-080859 | A | 3/2005 |
| JP | 2008-173286 | | 7/2008 |
| JP | 2008-295930 | A | 12/2008 |
| JP | 2009-106667 | A | 5/2009 |
| JP | 2009-153841 | A | 7/2009 |
| JP | 2009-153913 | A | 7/2009 |
| JP | 2009-207698 | A | 9/2009 |
| JP | 2009-297096 | | 12/2009 |
| JP | 2010-011911 | A | 1/2010 |
| JP | 2012-011056 | A | 1/2012 |
| JP | 5410897 | B2 | 2/2014 |
| JP | 2014-124471 | A | 7/2014 |
| JP | 2014-124477 | A | 7/2014 |
| JP | 2014-198178 | A | 10/2014 |
| JP | 2014-198180 | A | 10/2014 |
| JP | 2014-207973 | A | 11/2014 |
| JP | 2015-154796 | A | 8/2015 |

* cited by examiner (a)

←Width Direction (Streachable Direction)→

(b)

(a) (b)

(a)

(b)

(a)

(b)

(c)

STRETCHABLE STRUCTURE FOR ABSORBENT ARTICLE AND DISPOSABLE DIAPER PANTS

TECHNICAL FIELD

The present invention relates to a stretchable structure for an absorbent article having a softer texture in an unstretched state and an underpants-type disposable diaper having such a stretchable structure.

BACKGROUND ART

For example, underpants-type disposable diapers are each provided with an outer member including a front body and a back body and an inner member including an absorber fixed to the inner face of the outer member, the front body and the back body of the outer member being bonded at two opposite side edges to define a waist opening and right and left leg openings. In an underpants-type disposable diaper, elongated resilient and elastic members, such as rubber threads, are stretched and fixed to various portions of the outer member in the circumferential direction to provide a stretchable structure in the direction around the waist for enhancement of the fit to the body. Some underpants-type disposable diapers provided with waist-edge resilient and elastic members along the edge of the waist opening in the width direction and under-waist resilient and elastic members along the width direction closer to the crotch portion than the waist-edge resilient and elastic members have a relatively tight fit to the body and are commonly used.

In contrast, typical tape-type disposable diapers have the following structure: tape-type disposable diapers each includes a crotch portion, a ventral portion extending to the front side of the crotch portion, a dorsal portion extending to the back side of the crotch portion, an absorber provided in an area including the crotch portion, fastening tapes protruding from both sides of the dorsal portion, and target tapes disposed on the external face of the ventral portion and attachable to the fastening tapes; and the fastening tapes extend from both sides of the waist to the external face of the ventral portion and are attachable to the target tapes, to fix the diaper to the body. Such tape-type disposable diapers are commonly used for babies and toddlers and for nursing care (adults). In general, the fit of tape-type disposable diapers around the waist is lower than that of underpants-type disposable diapers. This is improved by stretching and fixing elongated resilient and elastic members, such as rubber threads, to the dorsal portion and the fastening tapes along the width direction, to provide a stretchable structure in the direction around the waist.

An improved stretchable structure, as illustrated in FIG. 17, is proposed (refer to PTL 1) in which multiple sheet bonding sections 20 are formed by intermittently bonding together two sheet layers 12H and 12S in the stretchable direction and the direction orthogonal to the stretchable direction; disposing multiple elongated resilient and elastic members 19 between the two sheet layers 12H and 12S without passing through the sheet bonding sections 20 (so as to pass through non-bonding sections); and fixing only the ends of each resilient and elastic member 19 to the sheet layers 12H and 12S. In the stretchable structure according to the traditional art, the sheet bonding sections 20 aligned in the longitudinal direction define grooves extending in the longitudinal direction, and two sheet layers protrude in opposite directions (from the front and back faces) by approximately the same height to define corrugations 80 in areas between the grooves, to provide a bellows structure as a whole. The corrugations 80 expand in the stretchable direction in a moderately stretched state, whereas the corrugations, which are thin in the stretchable direction, are continuously aligned in directions orthogonal to the stretchable direction, the material for the corrugations is folded over with a small radius of curvature at the tops of the corrugations to form creases, and the corrugations having such creases are aligned at the same height and close to each other in an unstretched state. The sheet bonding sections 20 illustrated in FIG. 17 are to be formed through welding of the sheet layers 12H and 12S. Alternatively, the sheet bonding sections 20 may be formed through the use of an adhesive, to define corrugations 80 having the same shape.

CITATION LIST

Patent Document

Patent Document 1: Japanese Unexamined Patent Application Publication No. 2005-080859

SUMMARY OF INVENTION

Technical Problem

Unfortunately, the stretchable structure according to the traditional art has a coarse texture when the two sheet layers are in a maximally contracted or unstretched state due to contraction of the resilient and elastic members, causing the product to feel coarse when handled by a user. The texture in an unstretched state affects the selection of products by the user, and thus, an improvement in texture is highly demanded.

An object of the present invention is to achieve a softer sense of touch of a product in an unstretched state.

Solution to Problem

The present invention, which provides solutions to the issues described above, is described below.
<The Invention of Claim 1>

A stretchable structure of an absorbent article, comprising:

two sheet layers that extend in a stretchable direction and an orthogonal direction orthogonal to the stretchable direction; and A plurality of elongated resilient and elastic members extending in the stretchable direction disposed at intervals in the orthogonal direction between the two sheet layers, wherein, the resilient and elastic members each have two fixed ends fixed to the two sheet layers in the stretchable direction, and a free section between the fixed ends, the free sections being unfixed to the two sheet layers, two adjacent free sections in the orthogonal direction define an inter-free region including at least one sheet bonding section, the two sheet layers being bonded at the at least one sheet bonding section, and When the two sheet layers are in a contracted state accompanied by contraction of the resilient and elastic members and conform to each other in a wave pattern.

Advantageous Effects

The inventors who conducted experiments on various stretchable structures discovered that disposing the sheet bonding sections continuously in the stretchable direction in the area between the free sections of the resilient and elastic members adjacent in the stretchable direction and the orthogonal direction can achieve a soft texture in an unstretched state. The inventors noticed that, as a basic principle, corrugations formed on the front and back faces of the two sheet layers conforming to each other in a wave pattern in an unstretched state have a soft texture.

Although the reason behind this is unclear, it is presumed that structural differences described in the following have an effect. In specific, in the structure according to the traditional art, corrugations thin in the stretchable direction in an unstretched state are continuous in the direction orthogonal to the stretchable direction; the material for the corrugations is folded over with a small radius of curvature at the tops of the corrugations to form creases; and the corrugations having such creases are aligned at the same height and close to each other. Thus, the corrugations are not readily compressed or distorted in the thickness direction. Moreover, the tops of the corrugations fold over with a small radius of curvature are coarse to the touch.

In contrast, in the present invention, when two sheet layers are in a contracted state, which includes an unstretched state, in response to the contraction of the resilient and elastic members, the two sheet layers conform with each other in a wave pattern in the inter-free regions and corrugations are formed on the front and back faces thereof. For the two sheet layers conforming with each other in a wave pattern, the tops of the corrugations can curve more gently than those of the traditional art because of increased stiffness simply due to the number of sheet layers and the difference in the curvature of the two sheet layers (the difference is particularly significant in a unstretched state). This causes a smooth hand feel and ready compression in the thickness direction, to enhance the softness of the texture. Moreover, in the two sheet layers conforming to each other in a gentle wave pattern, the distance increases between adjacent peaks and adjacent troughs of the wave pattern in the stretchable direction. This reduces the effect of the adjacent peaks and the adjacent troughs respectively supporting each other when the wave pattern is compressed or distorted in the thickness direction. This also is presumed to contribute to a softer texture. In the case where the front and back faces of a smooth material are pinched between fingers, a double layered material feels smoother than a single layered material, even if the material is the same. This is because the frictional resistance between the fingers or between a finger and the material is smaller than the frictional resistance between the layers of the material, and thus low frictional resistance (smoothness) is sensed when a double layered material is pinched. The two sheet layers conforming to each other are presumed to enhance the sense of smoothness.

In the present invention, the resilient and elastic members have high flexibility relative to the two sheet layers. Thus, the loss of stretching force is small, and natural contraction is achieved even if the stiffness of the sheet layers is uneven (for example, if the fiber density of the non-woven fabric of the sheet layers is uneven). Thus, the volume of the resilient and elastic members to be used can be reduced compared to that in the traditional art.

<The Invention of Claim 2>

The stretchable structure of an absorbent article, according to claim 1, wherein, the at least one sheet bonding section comprises multiple sheet bonding sections disposed in the inter-free region at intervals in the stretchable direction and the orthogonal direction, and the area rate of the sheet bonding sections gradually decreases toward the sides of the inter-free region in the orthogonal direction.

Advantageous Effects

In each inter-free region, the flexibility of the two sheet layers increases toward the center in the orthogonal direction. Thus, it is preferred to increase the area rate of the sheet bonding sections (the rate of the area of the sheet bonding sections to a unit area) and enhance the unity of the two sheet layers because the conforming state of the two sheet layers is barely distorted. At the edges of the inter-free regions in the orthogonal direction (i.e., in the vicinity of the resilient and elastic members), the resilient and elastic members hinder the approximation of the two sheet layers. Thus, for the sheet layers to absorb the hindering effect of the resilient and elastic members and independently deform (contract or bend) so that the sheet layers conform to each other, it is preferred that the area rate of the sheet bonding sections be small and the flexibility of the sheet layers be high.

<The Invention of claim 3>

The stretchable structure of an absorbent article, according to claim 2, wherein, the inter-free region comprises three portions having equal widths in the orthogonal direction in an unfolded state, the three portions comprising a central portion and two side portions positioned on the two sides of the central portion in the orthogonal direction, and the area rate of the sheet bonding sections in the side portions is 20% or less of the area rate of the sheet bonding sections in the central portion.

Advantageous Effects

For a configuration in which the area rate of the sheet bonding sections gradually decreases toward the two sides of each inter-free region in the orthogonal direction, the level of variation in the area rate of the sheet bonding sections can be appropriately determined. Usually, it is preferred that the area rate be within the range described in this aspect.

<The Invention of Claim 4>

The stretchable structure of an absorbent article, according to one of claims 1 to 3, wherein the resilient and elastic members comprise three or more resilient and elastic members disposed at intervals in the orthogonal direction, the resilient and elastic members defining multiple inter-free regions therebetween in the orthogonal direction, and the inter-free regions each include the sheet bonding sections intermittently disposed in the stretchable direction, a partial or entire group of the sheet bonding sections disposed in two adjacent inter-free regions in the orthogonal direction is substantially continuous along the stretchable direction.

Advantageous Effects

Although the sheet bonding sections may be disposed in any pattern as long as the two sheet layers conform with each other in a wave pattern, in the present invention, the sheet bonding sections can be disposed intermittently in the stretchable direction in each inter-free region and substantially continuously in the stretchable direction in two adjacent inter-free regions, as described in this aspect, to reduce the number of substantially continuous portions of the sheet bonding sections, thereby enhancing softness.

The sheet bonding sections "substantially continuous in the stretchable direction" are continuous (without disruption) on the target region in at least the direction orthogonal to the stretchable direction (parallel to the two sheet layers in an unfolded state and orthogonal to the resilient and elastic members), and, to this extend, include not only the sheet bonding sections continuous in the stretchable direction (the two sheet layers continuously bonded in the stretchable direction) but also the sheet bonding sections intermittently disposed in the stretchable direction (the two sheet layers intermittently bonded in the stretchable direction).

<The Invention of claim 5>

A stretchable structure of an absorbent article, including:

two sheet layers that extend in a stretchable direction and an orthogonal direction orthogonal to the stretchable direction; and elongated resilient and elastic members extending in the stretchable direction disposed at intervals in the orthogonal direction between the two sheet layers, wherein, the resilient and elastic members each have two fixed ends fixed to the two sheet layers in the stretchable direction, and a free section between the fixed ends, the free sections being unfixed to the two sheet layers, two adjacent free sections in the orthogonal direction define an inter-free region including at least one sheet bonding section, the two sheet layers being bonded at the at least one sheet bonding section, and in the inter-free regions, the sheet bonding sections is substantially continuous along the stretchable direction.

Advantageous Effects

As described above, the inventors, who conducted experiments on various stretchable structures, discovered that disposing the sheet bonding sections continuously in the stretchable direction in the area between the free sections of the resilient and elastic members adjacent in the stretchable direction and the orthogonal direction can achieve a soft texture in an unstretched state. This result contradicted the common belief that an increase in continuity of the sheet bonding sections, i.e., an increase in the density of the sheet bonding sections causes stiffness. In this experiment, each sheet bonding sections were actually formed by welding two sheet materials. The individual welded portions were harder than the unwelded portions. However, the surface having a wave pattern in an unstretched state was very soft to the touch. This is also apparent from the experimental results described below.

This is because of the reasons described above. The sheet bonding sections substantially continuous in the stretchable direction cause the two sheet layers to deform such that the sheet layers conform to each other. Thus, the texture in the unstretched state is soft.

As described above, the sheet bonding sections "substantially continuous in the stretchable direction" are continuous (without disruption) on the inter-free region in at least the direction orthogonal to the stretchable direction (parallel to the two sheet layers in an unfolded state and orthogonal to the resilient and elastic members), and, to this extend, include not only the sheet bonding sections continuous in the stretchable direction (the two sheet layers continuously bonded in the stretchable direction) but also the sheet bonding sections intermittently disposed in the stretchable direction (the two sheet layers intermittently bonded in the stretchable direction).

<The Invention of Claim 6>

The stretchable structure of an absorbent article, according to claim 5, wherein the sheet bonding sections in the inter-free regions are disposed to define multiple arrays extending in the stretchable direction, the multiple arrays are disposed at intervals in the orthogonal direction, sheet bonding sections in each first array of the multiple arrays and sheet bonding sections in a second array adjacent to the first array of the multiple arrays are disposed in a staggered pattern in the orthogonal direction, and an overlapping width in the stretchable direction of the sheet bonding sections in the first and second arrays is larger than an interval between the bonding sections in the first and second arrays in the orthogonal direction.

Advantageous Effects

As described above, the sheet bonding sections may be continuous in the stretchable direction, but in such a case, a reduction in softness is inevitable. In the case where the sheet layers composed of non-woven fabric or the like are fused to form continuous lines, the sheet layers readily tear along the bonding sections. Thus, it is preferred that the sheet bonding sections be intermittently dispose in the stretchable direction. In the case where the sheet bonding sections are intermittently disposed in the stretchable direction, the sheet bonding sections can be disposed substantially continuously in a multi-array configuration, as described in this aspect. The substantially continuous sheet bonding sections in a multi-array configuration are smaller and softer than those in a single array configuration, when the sheet bonding sections are compared under identical condition. Moreover, sufficient bonding strength for bonding can be achieved because many sheet bonding sections are used for bonding.

<The Invention of Claim 7>

The stretchable structure of an absorbent article, according to claim 6, wherein, in the stretchable direction, the sheet bonding sections have a maximum length within a range of 0.5 to 5.0 mm, in the stretchable direction, the sheet bonding sections in each array have an interval 0.1 to 0.9 times the maximum length of each of the sheet bonding sections in the stretchable direction, and the overlapping width in the stretchable direction of the sheet bonding sections in the first and second arrays of the multiple arrays is 0.2 times or more the interval in the orthogonal direction of the sheet bonding sections in the first and second arrays.

Advantageous Effects

In a case where multiple arrays of the sheet bonding sections are disposed as described above, it is preferred that the dimensions and the intervals of the sheet bonding sections be within the ranges described in this aspect.

<The Invention of Claim 8>

The stretchable structure of an absorbent article, according to claim 6 or 7, wherein the sheet bonding sections in the multiple arrays are disposed such that portions of the sheet bonding sections in in each first array of the multiple arrays the orthogonal direction overlap with portions of the sheet bonding sections in a second array adjacent to the first array in the orthogonal direction.

Advantageous Effects

In a case where multiple arrays of the sheet bonding sections are disposed as described above, the sheet bonding sections in adjacent arrays can overlap in the orthogonal direction, as described in this aspect, to achieve a higher stability in the shape of the corrugations according to the present invention.

<The Invention of Claim 9>

The stretchable structure of an absorbent article, according to one of claims 1 to 8, wherein the two sheet layers have a bending resistance in the stretchable direction higher than the bending resistance in the orthogonal direction.

Advantageous Effects

It is preferred that such sheet layers be used so that the tops of the corrugations readily define gentle curves.

<The Invention of Claim 10>

The stretchable structure of an absorbent article, according to one of claims 1 to 9, wherein, in an unfolded state, unbonded regions free from the sheet bonding sections are continuously disposed in the width direction on at least the two sides of the respective inter-free regions in the orthogonal direction, the unbonded regions being disposed over the entire width of the respective inter-free regions.

Advantageous Effects

In the configuration according to this aspect, the free sections of the resilient and elastic members are freely shiftable in the front-back direction (the direction orthogonal to the stretchable direction) within the areas between the sheet bonding sections, thereby providing a stretchable structure having excellent fit.

<The Invention of claim 11>

The stretchable structure of an absorbent article, according to claim 10, wherein each of the unbonded regions has a length within a range of 4 to 20 mm in the orthogonal direction.

Advantageous Effects

It is preferred that the dimensions of the unbonded regions be within the range described in this aspect to prevent the corrugations extending in the direction orthogonal to the stretchable direction and the orthogonal direction from readily deforming into irregular shapes due to collision of adjacent corrugations, for example.

<The Invention of Claim 12>

The stretchable structure of an absorbent article, according to one of claims 1 to 11, wherein
the resilient and elastic members comprises three or more resilient and elastic members disposed at intervals in the orthogonal direction, the resilient and elastic members defining multiple inter-free regions therebetween in the orthogonal direction, and
the inter-free regions each include the sheet bonding sections.

Advantageous Effects

In the case where three or more of the resilient and elastic members are disposed at intervals in the orthogonal direction, the sheet bonding sections may not be disposed in all of the inter-free regions adjacent in the orthogonal direction. In such a case, the free sections of the resilient and elastic members are shiftable in the orthogonal direction. This may cause the free sections of adjacent resilient and elastic members to come into contact and hinder smooth stretching or two of the resilient and elastic members to align side by side and leave marks on the skin of the wearer. Excessively large intervals of the sheet bonding sections hinder the conforming state of the two sheet layers. Thus, it is preferred that the stretchable structure have the configuration according to this aspect.

<The Invention of Claim 13>

An underpants-type disposable diaper including:
an outer member including a front body and a back body, and
an inner member disposed on the inner face of the outer member and including an absorber, wherein,
side seal portions provided by bonding the two side edges of the outer member of the front body and the respective side edges of the outer member of the back body constitute an annular waist portion, a waist opening, and left and right leg openings, and
the stretchable structure of the absorbent article according to one of claims 1 to 12 is disposed in an area of the outer member including at least the two exteriors of the inner member in the width direction, such that the stretchable direction of the stretchable structure is aligned with the width direction.

Advantageous Effects

As described above, the stretchable structure according to the present invention is suitable for areas in the outer member of an underpants-type disposable diaper, the areas being disposed at least on the two exteriors of the inner member in the width direction.

<The Invention of Claim 14>

An underpants-type disposable diaper including:
an outer member including a front body and a back body which are separated or integrated; and
an inner member including an absorber, the inner member disposed in a lateral intermediate portion extending from the inner face of the outer member of the front body to the inner face of the outer member of the back body, wherein,
the two side edges of the outer member of the front body is bonded to the respective side edges of the outer member of the back body, to constitute a waist opening and left and right leg openings,
the outer member comprises:
 a non-stretchable region that is disposed in a lateral intermediate area and extends in the front-back direction including the absorber; and
 intermittent stretchable regions disposed on the two exteriors of the non-stretchable region in the width direction,
the intermittent stretchable regions are disposed such that the stretchable direction of the stretchable structure of an absorbent article according to one of claims 1 to 12 aligns with the width direction,
the non-stretchable region comprises two sheet layers continuing from the intermittent stretchable regions and residual resilient and elastic members, the residual resilient and elastic members including at least one of residual pieces remaining between the two sheet layers and continuing from resilient and elastic members in the intermittent stretchable regions and cut pieces of the resilient and elastic members discontinuous from the resilient and elastic members in the intermittent stretchable regions,
the residual resilient and elastic members are unfixed to the two sheet layers, and
in the non-stretchable region, the two sheet layers are bonded at the sheet bonding sections substantially continuous in the width direction on the two sides of the residual resilient and elastic members in the front-back direction.

The waist region and the intermediate region of the outer member overlap the front-back area including the absorber and include inner-outer fixing portions for fixing the inner member to the outer member. Thus, even if the resilient and elastic members are disposed in the front-back area including the absorber, the stretching ability of the resilient and elastic members is limited by the stiffness of the absorber. Contraction of the absorber in the width direction may impair the wearing feeling and the pleasant appearance and cause twisting and breaking of the absorber, thereby leading to a decrease in the absorption ability.

Thus, it is common in the traditional art to continuously dispose the resilient and elastic members in the width direction and form a non-stretchable region in which the contraction force is not applied to the absorber in the width direction (i.e., elasticity is nullified) while intermittent stretchable regions are preserved on both sides of the non-stretchable region, by snicking substantially the entire portion of each resilient and elastic member overlapping the absorber or cutting each resilient and elastic members at an intermediate position in the width direction. In such a non-stretchable region, residual resilient and elastic members including residual pieces continuing from the resilient and elastic members in the intermittent stretchable regions and/or cut pieces of the resilient and elastic members discontinuous from the resilient and elastic members in both of the intermittent stretchable regions remain between the two sheet layers. These residual resilient and elastic members may be unfixed to the two sheet layers, to completely cancel out the contraction force after cutting.

However, the formation of the non-stretchable region through cutting of the resilient and elastic members allows the residual resilient and elastic members to readily shift in an irregular manner and even largely shift in the front-back direction after passing between adjacent sheet bonding sections in the width direction, unless, in the non-stretchable region, the sheet bonding sections are intermittently disposed in the width and the front-back directions and the residual resilient and elastic members are fixed, as described in the traditional art. The largely shifted residual resilient and elastic members may falsely appear to be foreign objects.

Thus, it is important to prevent the shift of the residual resilient and elastic members due to cutting of the resilient and elastic members, thereby preventing impairment of a pleasant appearance.

In contrast, in this aspect of the present invention, the residual resilient and elastic members are unfixed to the two sheet layers. Thus, the contraction force of the residual resilient and elastic members applied to the two sheet layers can be completely cancelled out. Furthermore, in the non-stretchable region, the two sheet layers are bonded at the two front-back sides of the residual resilient and elastic members by the sheet bonding sections substantially continuous in the width direction, thereby limiting the residual resilient and elastic members from shifting in the front-back direction within the areas between the sheet bonding sections on the two front-back sides of the residual resilient and elastic members. This prevents a large shift that may impair a pleasance appearance.

The sheet bonding sections "substantially continuous in the stretchable direction" are continuous (not disrupted) on at least the direction orthogonal to the stretchable direction (parallel to the two sheet layers in an unfolded state and orthogonal to the resilient and elastic members), and, to this extent, include not only the sheet bonding sections continuous in the stretchable direction (the two sheet layers are continuously bonded in the stretchable direction) but also the sheet bonding sections intermittently disposed in the stretchable direction (the two sheet layers are intermittently bonded in the stretchable direction).

<The Invention of Claim 15>

The underpants-type disposable diaper according to claim 14, wherein, the sheet bonding sections in the non-stretchable region are disposed at intervals to define multiple arrays extending in the width direction, the multiple arrays are disposed in the front-back direction, the sheet bonding sections in each first array of the multiple arrays overlap with the sheet bonding sections in the width direction in a second array adjacent to the first array in the front-back direction, and an overlapping width in the width direction of the sheet bonding sections in the first array and the sheet bonding sections in the second array adjacent to the first array in the front-back direction is larger than the interval between the first and second sheet bonding sections in the front-back direction.

Advantageous Effects

As described above, although the sheet bonding sections may be continuous in the width direction, it is preferred that the sheet bonding sections be intermittently disposed in the width direction to avoid reduction in softness. In the case where the sheet bonding sections are intermittently disposed in the width direction, the sheet bonding sections can be disposed substantially continuously in a multi-array configuration, as described in this aspect. The substantially continuous sheet bonding sections in a multi-array configuration are smaller and softer than those in a single array configuration, when the sheet bonding sections are compared under identical condition. Moreover, sufficient bonding strength for bonding can be achieved because many sheet bonding sections are used for bonding.

<The Invention of Claim 16>

The underpants-type disposable diaper according to claim 15, wherein, in the non-stretchable region, the sheet bonding sections have a maximum length within a range of 0.5 to 5.0 mm in the width direction, the sheet bonding sections in each array have an interval in the width direction of 0.1 to 0.9 times the maximum length of the sheet bonding sections in the width direction, and the overlapping width in the width direction of the sheet bonding sections in the first array and the sheet bonding sections in the second array in the front-back direction is 0.2 times or more the interval in the front-back direction of the first sheet bonding section and the second sheet bonding section.

Advantageous Effects

In the case where multiple arrays of the sheet bonding sections are disposed, as described above, it is preferred that the dimensions and intervals of the sheet bonding sections be within the range described in this aspect.

<The Invention of Claim 17>

The underpants-type disposable diaper according to claim 15 or 16, wherein, in the non-stretchable region, the sheet bonding sections in the multiple arrays are disposed such that portions of the sheet bonding sections in the front-back direction in the first array overlap with portions of the sheet bonding sections in the front-back direction in the second array in the front-back direction.

Advantageous Effects

In the case where multiple arrays of the sheet bonding sections are disposed as described above, an overlap of the sheet bonding sections in adjacent arrays in the front-back direction, as in this aspect, increases the continuity of the sheet bonding sections.

<The Invention of claim 18>

The underpants-type disposable diaper according to one of claims 14 to 17, wherein the sheet bonding sections are disposed in a uniform pattern over the entire width of the outer member.

Advantageous Effects

The sheet bonding sections disposed in a uniform pattern over the entire width of the outer member in this way leads to ready and stable production of the outer member and simplification of the production device. Moreover, by disposing the sheet bonding sections in a uniform pattern over the entire width of the outer member, the inter-free regions in the intermittent stretchable regions are also bonded by the sheet bonding sections substantially continuous in the width direction. In such a case, the texture in the unstretched state is soft.

<The Invention of Claim 19>

The underpants-type disposable diaper according to one of claims 14 to 18, wherein at at least the exteriors of the intermittent stretchable regions adjacent to the center in the width direction, the two sheet layers are bonded with a hot-melt adhesive continuously extending over the entire intermittent stretchable regions in the front-back direction, and the hot-melt adhesive constitutes fixed ends of the resilient and elastic members.

Advantageous Effects

By forming the fixed ends of the resilient and elastic members at at least the exteriors of the intermittent stretchable regions adjacent to the center in the width direction with a hot-melt adhesive continuing in the front-back direction, the spaces between the two sheet layers in the intermittent stretchable regions are seals at the sides of the non-stretchable region in the width direction. This can prevent impairment of the pleasing appearance due to a shift of the residual resilient and elastic members to the intermittent stretchable regions.

Advantages Effects Of Invention

As described above, the present invention is advantageous in that a softer sense of touch of a product is achieved in an unstretched state.

DESCRIPTION OF EMBODIMENTS

Figure 1:
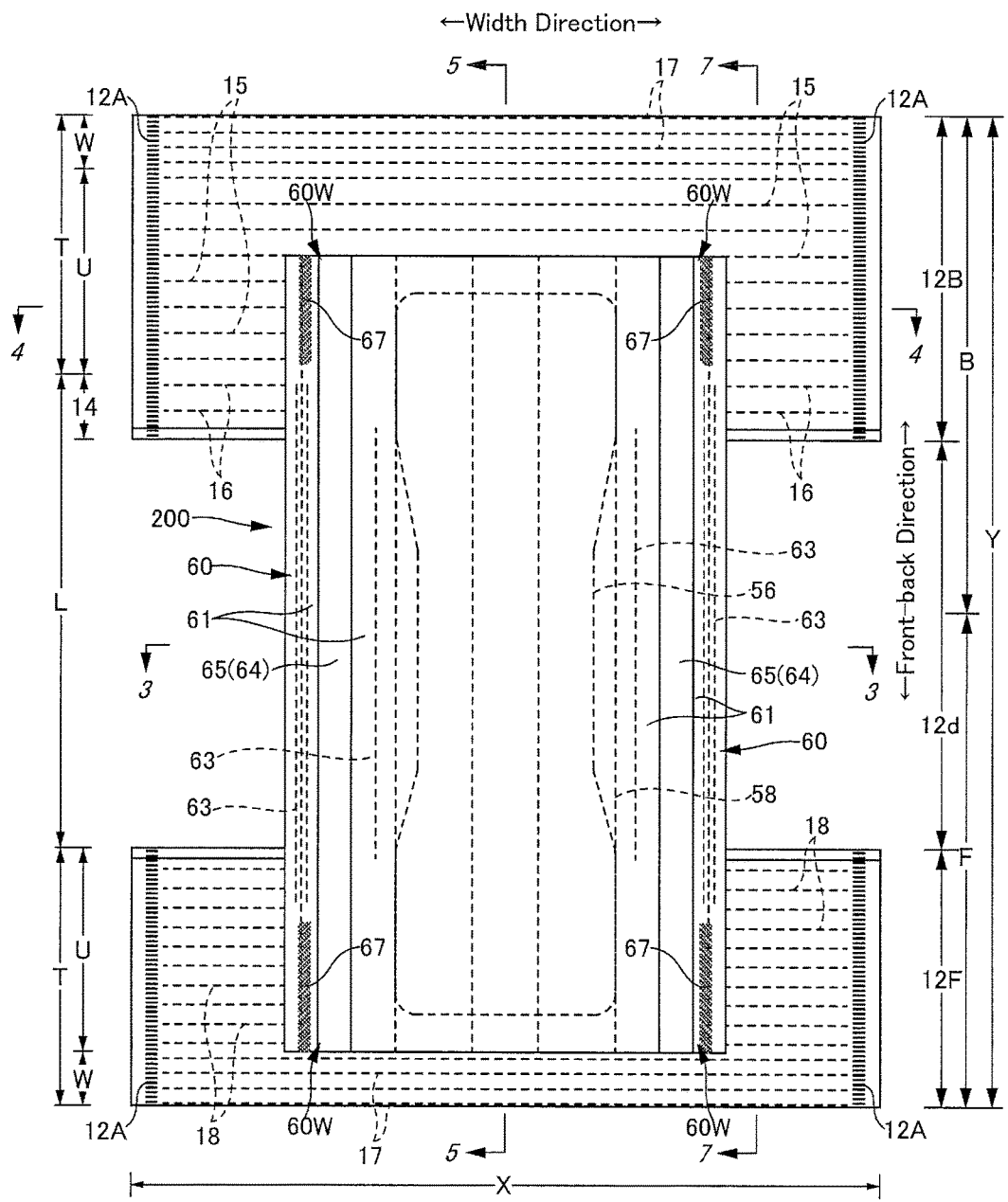
FIG. 1 is a plan view of the inner face of an underpants-type disposable diaper in an unfolded state.

Embodiments of the present invention will now be described in detail with reference to the accompanying drawings.

FIGS. 1 to 6 illustrate an example underpants-type disposable diaper. The dot patterns in the cross-sections indicate adhesive patterns serving as bonding means of components on the front and back sides. The adhesive patterns are formed through solid, bead, curtain, summit, or spiral application of a hot-melt adhesive or the like, and the fixed portions of the resilient and elastic members are formed through such application of the adhesive and/or application of the adhesive with a comb gun or a Surewrap nozzle to the circumferential face of the resilient and elastic members. Examples of other bonding means of components may include a fixing means by material welding, such as heat sealing or ultrasonic sealing.

The underpants-type disposable diaper according to this embodiment includes outer members 12F and 12B of a front body F and a back body B respectively and an inner member 200 provided on the inner faces of the outer members 12F and 12B and extends across the front body F and the back body B through the crotch portion. The two side edges of the outer member 12F of the front body F are bonded to the respective side edges of the outer member 12B of the back body B, to form side seal portions 12A. The reference sign Y indicates the entire length of the diaper in an unfolded state (the longitudinal length from the edge of the waist opening WO of the front body F to the edge of the waist opening WO of the back body B), and the reference sign X indicates the entire width of the diaper in an unfolded state.

The inner member 200 absorbs and retains excretion, such as urine, and the outer members 12 support the inner member 200 on the body of the wearer. In this embodiment, the upper opening of the outer members 12F and 12B define the waist opening WO through which the trunk of the wearer passes, and the lower edges of the outer members 12F and 12B and the side edges of the inner member 200 define leg openings LO through which the legs pass at both sides of the inner member 200 in the width direction.

The underpants-type disposable diaper according to this embodiment includes a waist region T defined as a front-back region including the side seal portions 12A (the longitudinal regions from the waist opening WO to the upper edges of the leg openings LO) and an intermediate region L defined as a front-back region forming the leg openings LO (the region between the longitudinal region including the side seal portion 12A of the front body F and the longitudinal region including the side seal portion 12A of the back body B). The waist region T can be conceptually separated into a "waist portion" W forming the edge of the waist opening and an "under-waist portion" U disposed below the waist portion W. Usually, in the case that the waist region T includes boundaries undergoing variations in expansion and contraction stress along the width direction (for example, variations in the thickness or the stretch rate of the resilient and elastic members), the area between the boundary closest to the waist opening WO and the waist opening WO is defined as the waist portion W. In the case that such boundaries are absent, the area between an absorber 56 or the inner member 200 and the waist opening WO is defined as the waist portion W. The longitudinal lengths of such portions depend on the dimensions of the product and can be appropriately determined. For example, the longitudinal length may be within the range of 15 to 40 mm for the waist portion W and 65 to 120 mm for the under-waist portion U. The two side edges of the intermediate region L are curved into a U-shape or C-shape to fit around the legs of the wearer and define openings through which the legs of the wearer pass. As a result, the underpants-type disposable diaper in an unfolded state has an overall shape similar to the outline of an hourglass.

(Outer Members)

Figure 9:
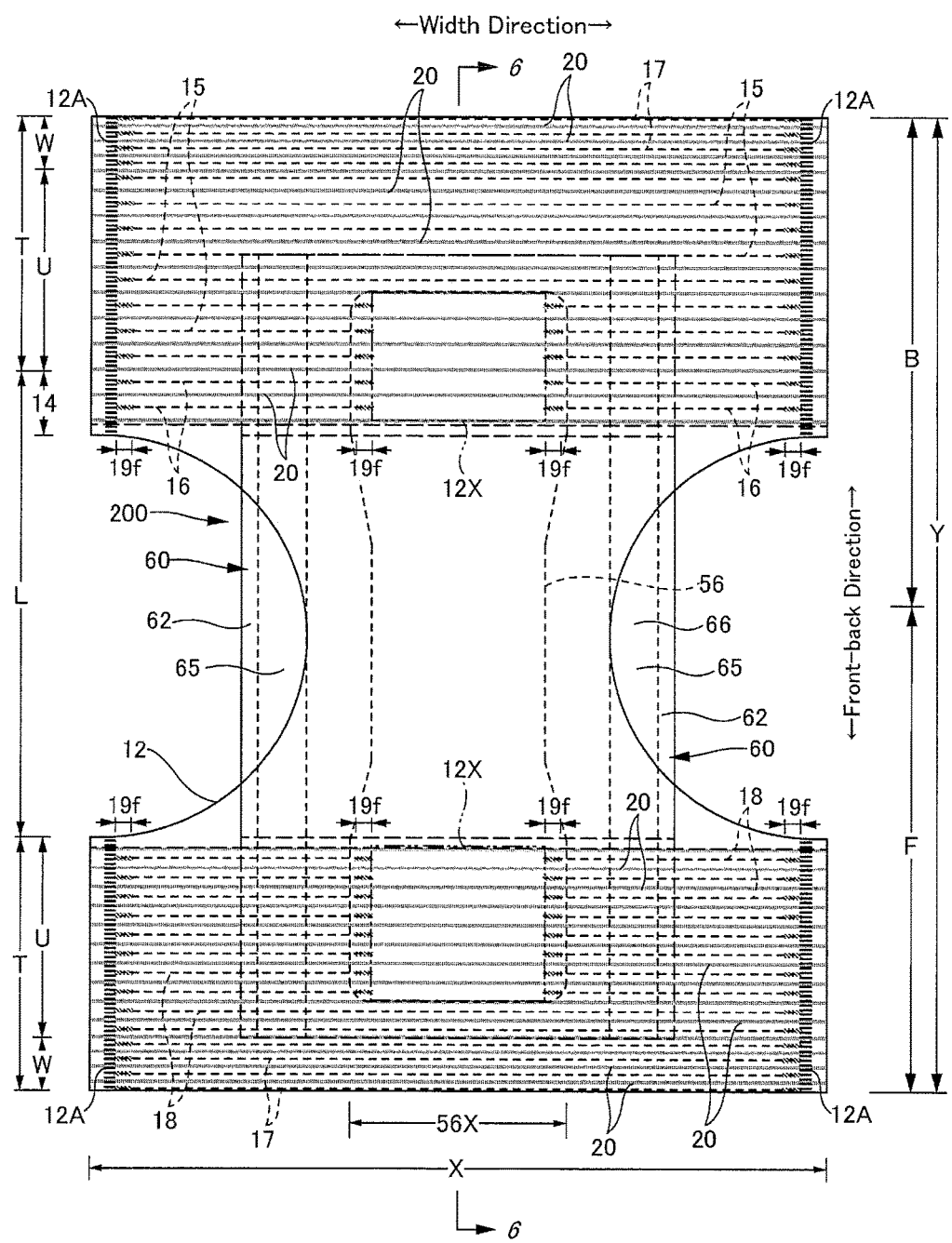
FIG. 9 is a plan view of the external face of the underpants-type disposable diaper in an unfolded state.

The outer members 12F and 12B, respectively, function as a front outer member 12F of the front body F and a back outer member 12B of the back body B. The front outer member 12F and the back outer member 12B are discontinuous or separated at the sides adjacent to the legs. The distance of separation 12d may be within the range of approximately 150 to 250 mm. Although not illustrated, a crotch cover sheet composed of non-woven fabric may be bonded to the entire inner member 200 or a section of the back face of the inner member 200 exposed through the separation (the section extending in the front-back direction of the exposed inner member 200 between the front outer member 12F and the back outer member 12B without reaching the front-back edges of the inner member 200 and extending in the width direction without reaching both side edges of the inner member 200, for example). Alternatively, the outer members 12 may be an integrated body of the front body F and the back body B through the crotch, as illustrated FIGS. 9 and 10. That is, the outer members 12F and 12B of the front body F and the back body B, respectively, are separated in the former configuration, whereas the outer members 12 of the front body F and back body B are integrated in the latter configuration.

The outer members 12F and 12B have waist portions, respectively, corresponding to the waist region T extending in the longitudinal direction. In this embodiment, the front outer member 12F has no portion corresponding to the intermediate region L, whereas the back outer member 12B has a gluteal cover portion 14 extends from the waist region T into the intermediate region L. Although not illustrated, the front outer member 12F may also be provided with an inguinal cover portion extending from the waist region T into the intermediate region L; the front outer member 12F may be provided with an inguinal cover portion and without a gluteal cover portion; or both the front outer member 12F and the back outer member 12B may be free from portions corresponding to the intermediate region L. In this embodiment, the lower edge of the gluteal cover portion 14 is a straight line extending in the width direction, like the lower edge of the front outer member 12F. Alternatively, the lower edge of the gluteal cover portion 14 may be curved such that the outer ends of the lower edge in the width direction are closer to the waist opening.

Figure 3:
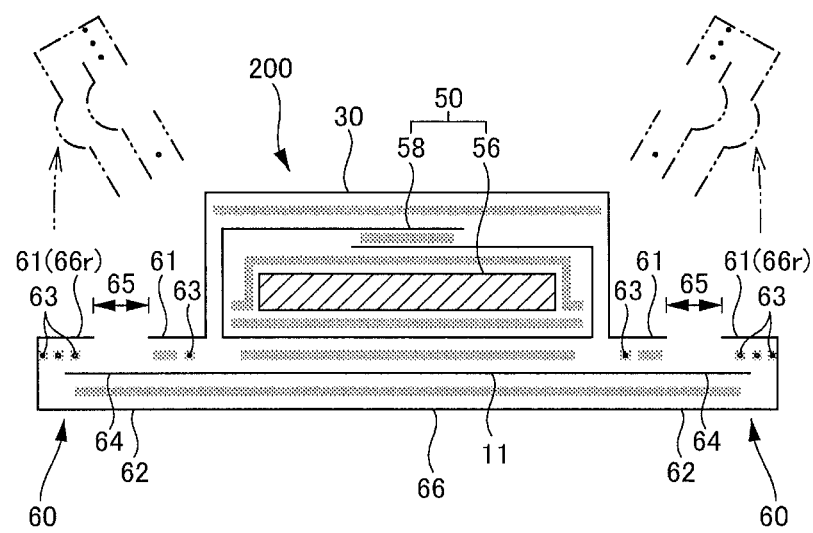
FIG. 3 is a cross-section taken along line 3-3 in FIG. 1.
Figure 4:
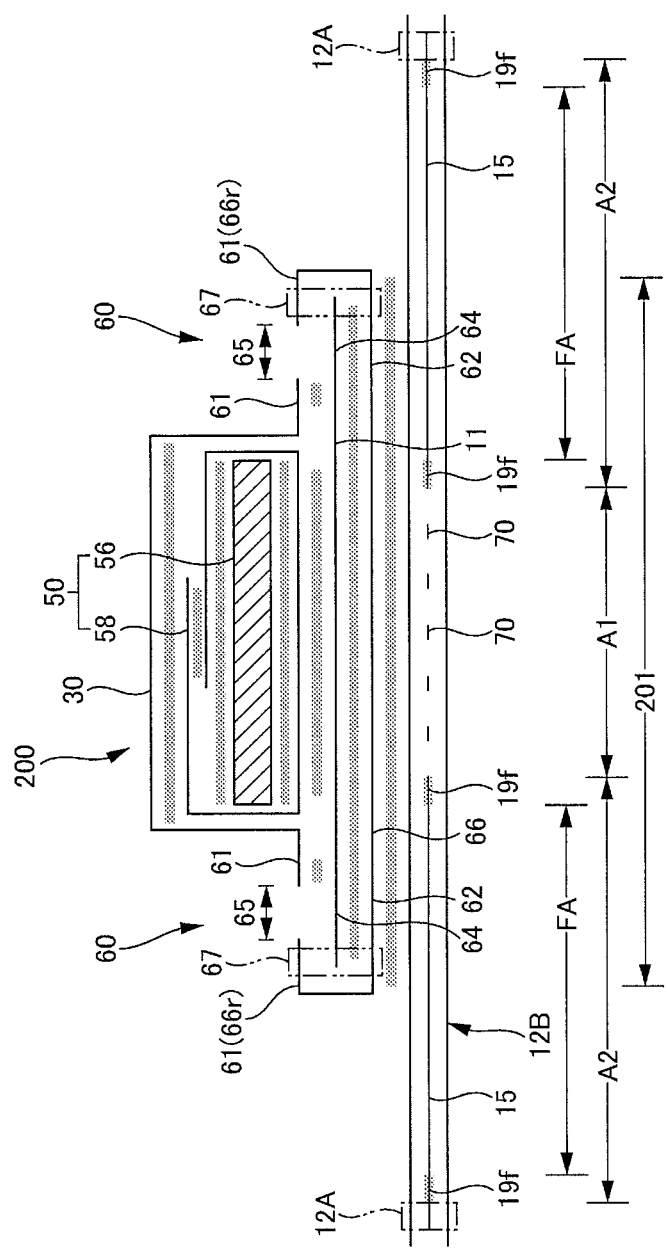
FIG. 4 is a cross-section taken along line 4-4 in FIG. 1.
Figure 5:
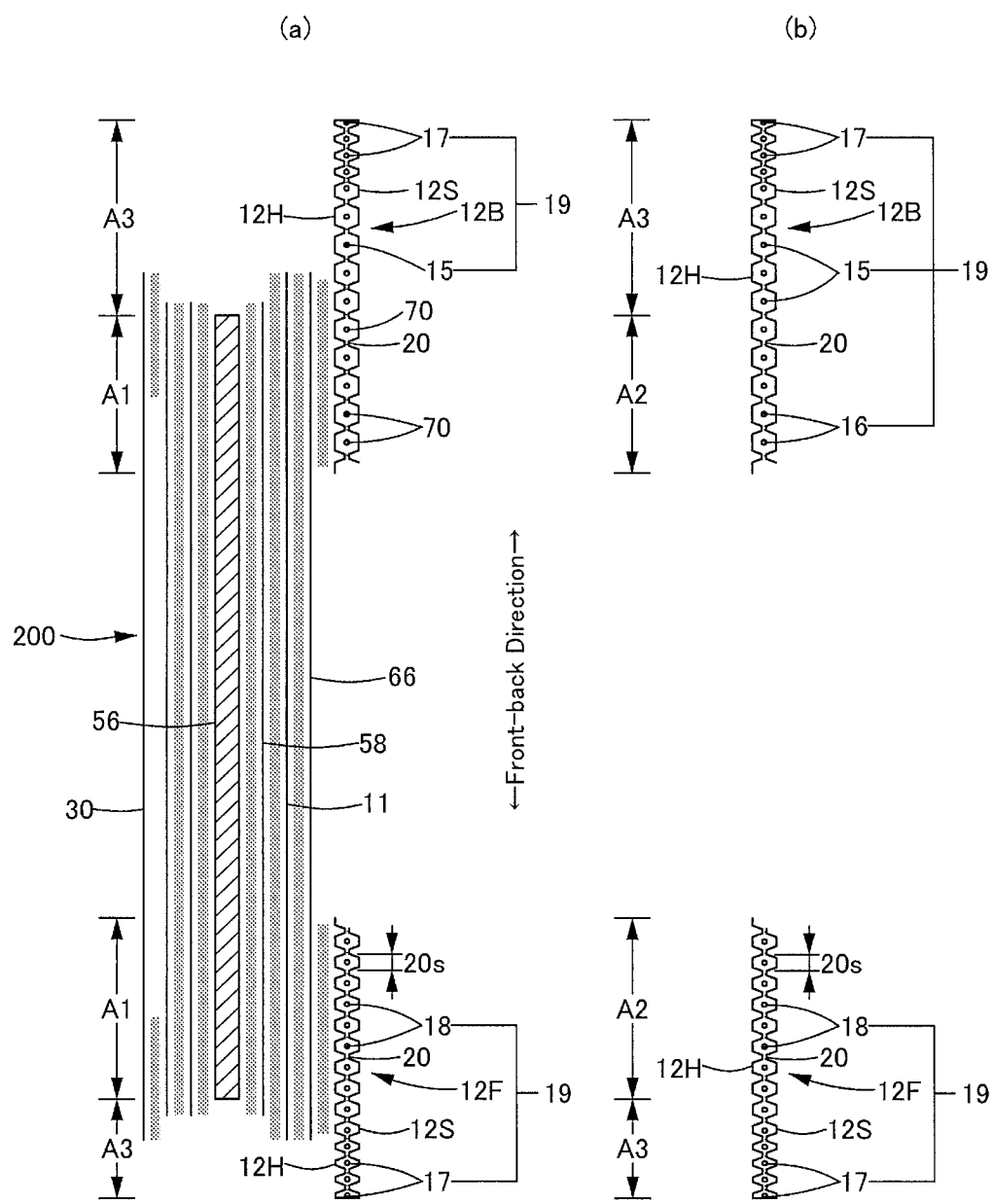
FIG. 5 is a cross-section taken along line 5-5 in FIG. 1.
Figure 10:
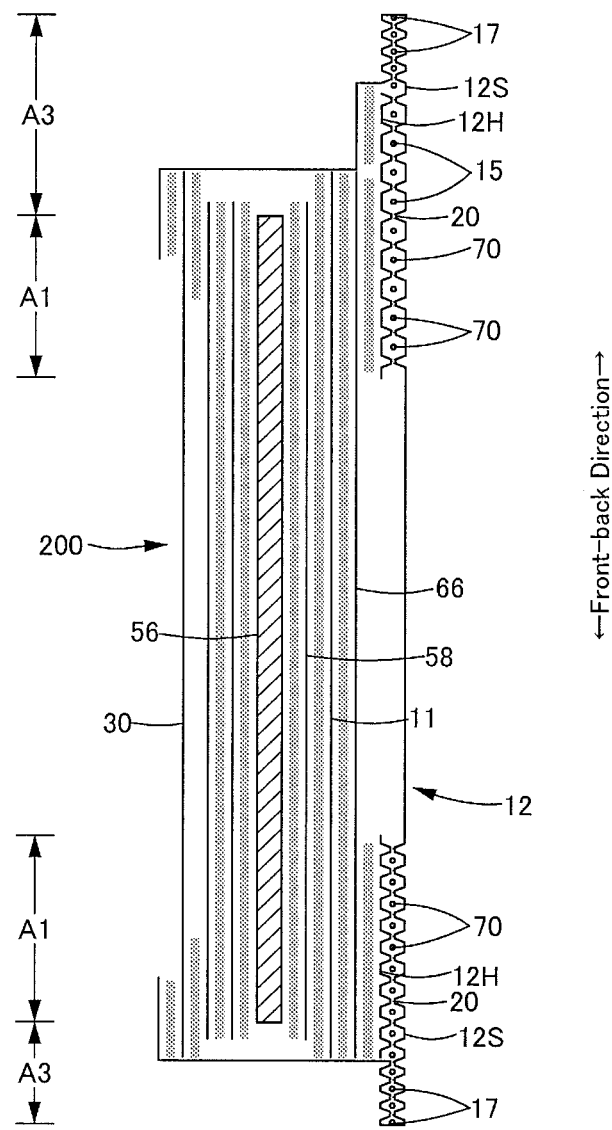
FIG. 10 is a cross-section taken along line 6-6 in FIG. 9.

The outer members 12F and 12B are each provided with an outer sheet layer 12S and an inner sheet layer 12H on the front face and back face, respectively, as illustrated in FIGS. 2 to 5. The outer sheet layer 12S and the inner sheet layer 12H are composed of a single sheet material folded such that the crease is positioned adjacent to the waist opening, as illustrated in FIG. 5. Alternatively, the outer sheet layer 12S and the inner sheet layer 12H may be composed of two sheet materials bonded together, as illustrated in FIG. 10. At least one of the outer sheet layer 12S and the inner sheet layer 12H may include a portion composed of a sheet material different from that of the other portions.

The outer sheet layer 12S and the inner sheet layer 12H may be composed of any sheet material, preferably non-woven fiber. The non-woven fiber may be composed of any raw fibers. Examples include synthetic fibers, such as olefin fibers i.e., polyethylene fibers and polypropylene fibers, polyester fibers, and polyamide fibers; recycled fibers, such as rayon and cupra; natural fibers, such as cotton; and mixed fibers and composite fibers composed of two or more of these fibers. If the sheet bonding sections 20 are to be formed through welding, non-woven fabrics composed of olefin fibers are preferred. The non-woven fabrics may be produced through any process. Examples of known processes include spunlacing, spunbonding, thermal bonding, melt blowing, needle punching, air through bonding, and point bonding. From a viewpoint of softness, a spundonded non-woven fabric composed of polypropylene fiber is particularly preferred for the outer sheet layer 12S and the inner sheet layer 12H. The outer sheet layer 12S and the inner sheet layer 12H may be composed of different sheet materials.

For use of non-woven fabric, the preferred fineness is within the range of approximately 1 to 3 dtex, and the preferred basis weight is within the range of approximately 10 to 30 g/m². Thus, the preferred total basis weight of the non-woven fabric of the outer members 12F and 12B is within the range of approximately 20 to 60 g/m². The average coefficient of surface friction MIU of the non-woven fabric based on Kawabata's Evaluation System for Fabrics (KES) is 0.30 or smaller, preferably within the range of 0.05 to 0.20 (in both the MD and CD); the deviation of the coefficient of surface friction MMD is 0.01 or smaller, preferably within the range of 0.003 to 0.008 (in both the MD and CD); and the thickness under a load of 0.5 g/cm² is within the range of 0.05 to 0.25 mm, preferably 0.10 to 0.20 mm. The MIU and the MMD can be measured with a Friction Tester KES-SE manufactured by Kato Tech Co., Ltd.

The outer members 12F and 12B have continuous stretchable regions A3 extending from the absorber 56 toward the waist opening continuously in the width direction; and non-stretchable regions A1 disposed in intermediate areas in the width direction and intermittent stretchable regions A2 disposed on both side of the respective non-stretchable regions A1 in the width direction, in the front-back region including the absorber 56. The elongated resilient and elastic members 19 (15 to 18), such as rubber threads, are fixed between the outer sheet layer 12S and the inner sheet layer 12H in the continuous stretchable region A3 and the intermittent stretchable regions A2 at a predetermined stretch rate in the width direction in a manner stretchable in the width direction (i.e., the width direction is the stretchable direction). The elongated resilient and elastic members 19 may be composed of either synthetic rubber or natural rubber. In part or all of the front-back region including the non-stretchable regions A1 and the intermittent stretchable regions according to this embodiment, the continuous stretchable regions A3 may be disposed over the entire width, or the front-back region included the non-stretchable regions A1 according to this embodiment may be expanded toward the waist or the crotch.

More specifically, in this embodiment, multiple waist resilient and elastic members 17 are stretched and continuously fixed over the entire width between the outer sheet layer 12S and the inner sheet layer 12H in the waist portion W of the outer members 12F and 12B, respectively, at predetermined intervals in the front-back direction at a predetermined stretch rate in the width direction. Among the waist resilient and elastic members 17, one or more of the members disposed in the regions adjoining the under-waist portion U may overlap the inner member 200 or may be disposed on the two sides in the width direction, avoiding the intermediate area in the width direction overlapping the inner member 200. Each waist resilient and elastic member 17 is preferably composed of approximately 3 to 22 rubber threads having a thickness within the range of approximately 155 to 1880 dtex, specifically 470 to 1240 dtex (synthetic rubber) (for natural rubber, the cross-section is within the range of approximately 0.05 to 1.5 mm², specifically 0.1 to 1.0 mm²) fixed at intervals within the range of approximately 5 to 20 mm, specifically 8 to 16 mm, at a stretch rate within the range of approximately 150% to 400%, specifically 220% to 320%. The waist resilient and elastic members 17 may have different thicknesses and stretch rates. For example, the thickness and stretch rate of the resilient and elastic members may differ in the upper and lower areas in the waist portion W.

Under-waist resilient and elastic members 15 and 18 composed of elongated resilient and elastic members are stretched and continuously fixed over the entire width of the outer members 12F and 12B, respectively, in areas of the under-waist portion U above and adjacent in the width direction of the respective non-stretchable regions A1, avoiding the non-stretchable regions A1, between the outer sheet layer 12S and the inner sheet layer 12H at predetermined intervals in the front-back direction and a predetermined stretch rate in the width direction. The under-waist resilient and elastic members 15 and 18 are each approximately 5 to 30 rubber threads having a thickness within the range of approximately 155 to 1880 dtex, specifically 470 to 1240 dtex (synthetic rubber) (for natural rubber, the cross-section is within the range of approximately 0.05 to 1.5 mm², specifically 0.1 to 1.0 mm²) fixed at intervals within the range of approximately 5 to 20 mm, specifically 8 to 16 mm, at a stretch rate within the range of approximately 200% to 350%, specifically 240% to 300%.

Multiple cover resilient and elastic members 16 composed of elongated resilient and elastic members are stretched and fixed over the entire width of areas adjacent to the relevant non-stretchable region A1 in the width direction, avoiding to the non-stretchable region A1, between the outer sheet layer 12S and the inner sheet layer 12H of the gluteal cover portion 14 of the back outer member 12B, at predetermined intervals in the front-back direction at a predetermined stretch rate in the width direction. Each cover resilient and elastic member 16 is preferably composed of approximately two to ten rubber threads having a thickness within the range of approximately 155 to 1880 dtex, specifically 470 to 1240 dtex (synthetic rubber) (for natural rubber, the cross-section is within the range of approximately 0.05 to 1.5 mm², specifically 0.1 to 1.0 mm²) at intervals within the range of approximately 5 to 20 mm, specifically 8 to 16 mm, at a stretch rate within the range of approximately 150% to 300%, specifically 180% to 260%. In the case that an inguinal cover portion is to be provided on the front outer member 12F, the cover resilient and elastic members 16 may be provided in a similar manner.

As in the intermittent stretchable regions A2 according to this embodiment, the resilient and elastic members 19 (the under-waist resilient and elastic members 15 and 18 and the cover resilient and elastic members 16 according to this embodiment) of the outer members 12F and 12B fixed in the areas adjacent to the non-stretchable regions A1, other than the non-stretchable regions A1, prevent contraction in the with direction of the absorber 56 in the non-stretchable regions A1. Thus, it is preferred that the non-stretchable regions A1 be defined as intermediate areas in the width direction partially or completely overlaying the absorber 56 in the width direction (preferably includes an entire inner-outer fixing portion 201) and the intermittent stretchable regions A2 are defined as areas adjacent to the non-stretchable regions A1 extending over the entire width from the sides of the non-stretchable regions A1 to the respective side seal portions 12A.

(Fixed Portion of Resilient and Elastic Members)

With reference to FIGS. 2, 9, and 11 to 14, the two ends in the width direction of each resilient and elastic member 19 in the continuous stretchable region A3 and the intermittent stretchable regions A2 are fixed ends 19f fixed to the outer sheet layer 12S and the inner sheet layer 12H, and the section between the fixed ends 19f is a free section 19m not fixed to the outer sheet layer 12S and the inner sheet layer 12H. The free section 19m of the resilient and elastic member 19 is freely stretchable in the width direction and shiftable in the front-back direction (the direction orthogonal to the stretchable direction) within the areas between the sheet bonding sections 20, as described below. In detail, with reference to the drawings, the fixed ends 19f of the resilient and elastic members 19 disposed adjacent in the width direction to areas of the outer members 12F and 12B partially or entirely overlaying the inner member 200 are the two ends of the respective resilient and elastic members 19 adjacent in the width direction to these areas, whereas the fixed ends 19f of the resilient and elastic members 19 disposed over the entire width of the outer members 12F and 12B are the two ends of the respective resilient and elastic members 19 in the width direction of the outer members 12F and 12B.

Figure 12:
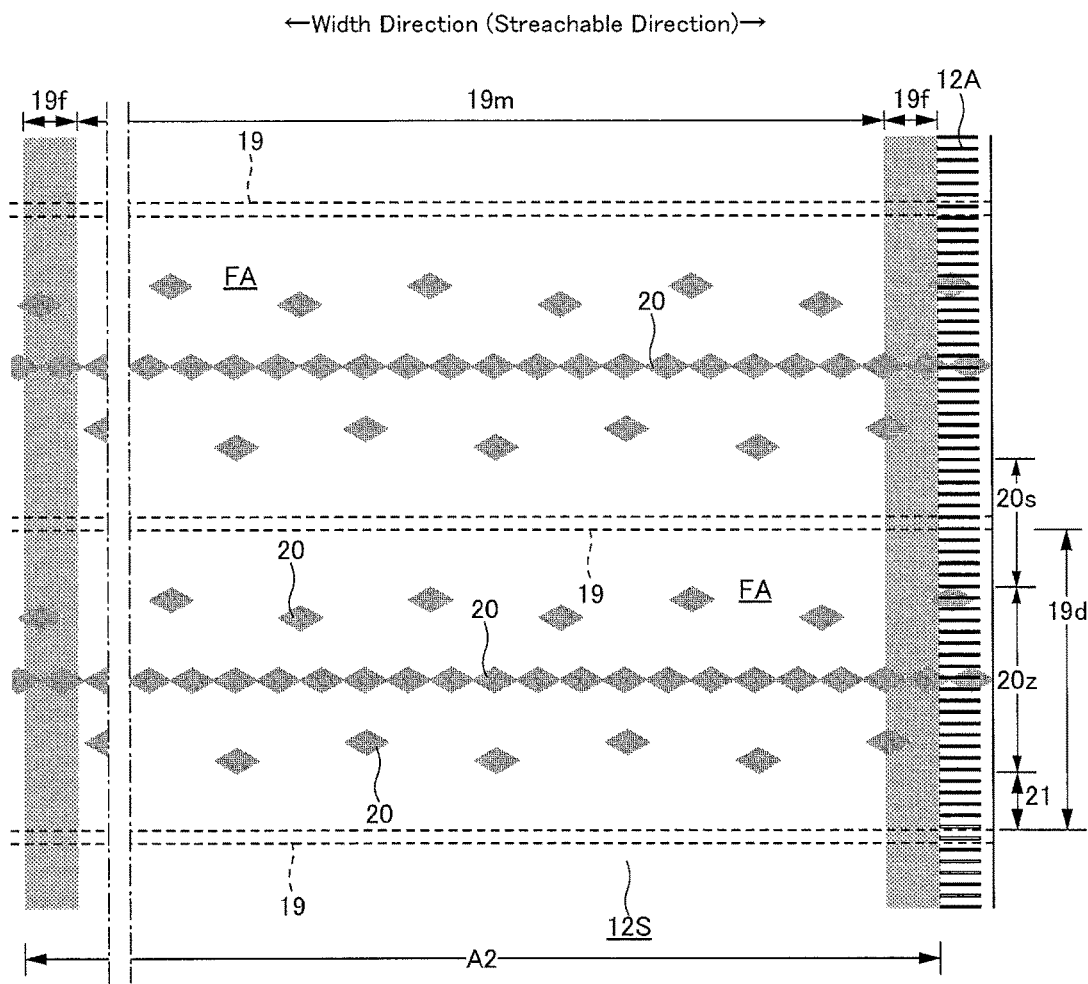
FIG. 12 is an enlarged plan view of essential components of the outer member in an unfolded state.
Figure 13:
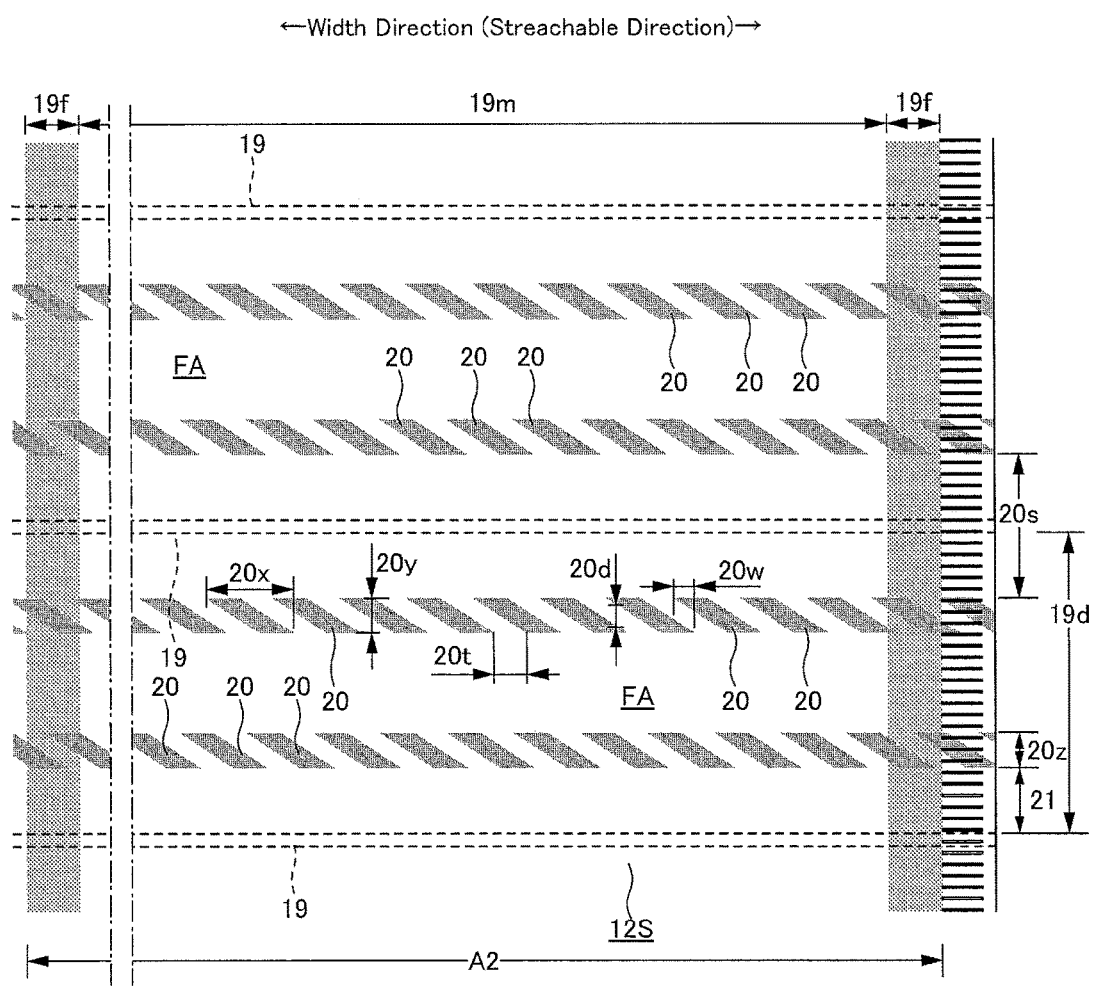
FIG. 13 is an enlarged plan view of essential components of the outer member in an unfolded state.

Any known fixing means may be used to fix the fixed ends 19f so as to fix the resilient and elastic members 19 to the outer sheet layer 12S and the inner sheet layer 12H. It is preferred to use a hot-meld adhesive. A hot-melt adhesive is applied to only the end portions of the resilient and elastic members 19, as illustrated in FIGS. 2, 9, 11, and 14. Alternatively, the hot-melt adhesive may be applied in a continuous pattern in the front-back direction across the ends of multiple resilient and elastic members 19, as illustrated in FIGS. 12 and 13. The hot-melt adhesive for fixing the fixed ends 19f is applied to at least one of the outer sheet layer 12S and the inner sheet layer 12H. Alternatively, the hot-melt adhesive may be applied to only the end portions of the resilient and elastic members 19 with an application means, such as a comb gun or a Surewrap nozzle, to only the circumferential surfaces of the end portions of the resilient and elastic members 19.

The fixed ends 19f adjacent to the side seal portions 12A preferably adjoin the side seal portions 12A, as illustrated in the drawings. Alternatively, the fixed ends 19f may be disposed remote from the side seal portions 12A toward the center in the width direction.

(Sheet Bonding Sections in Stretchable Regions)

Figure 2:
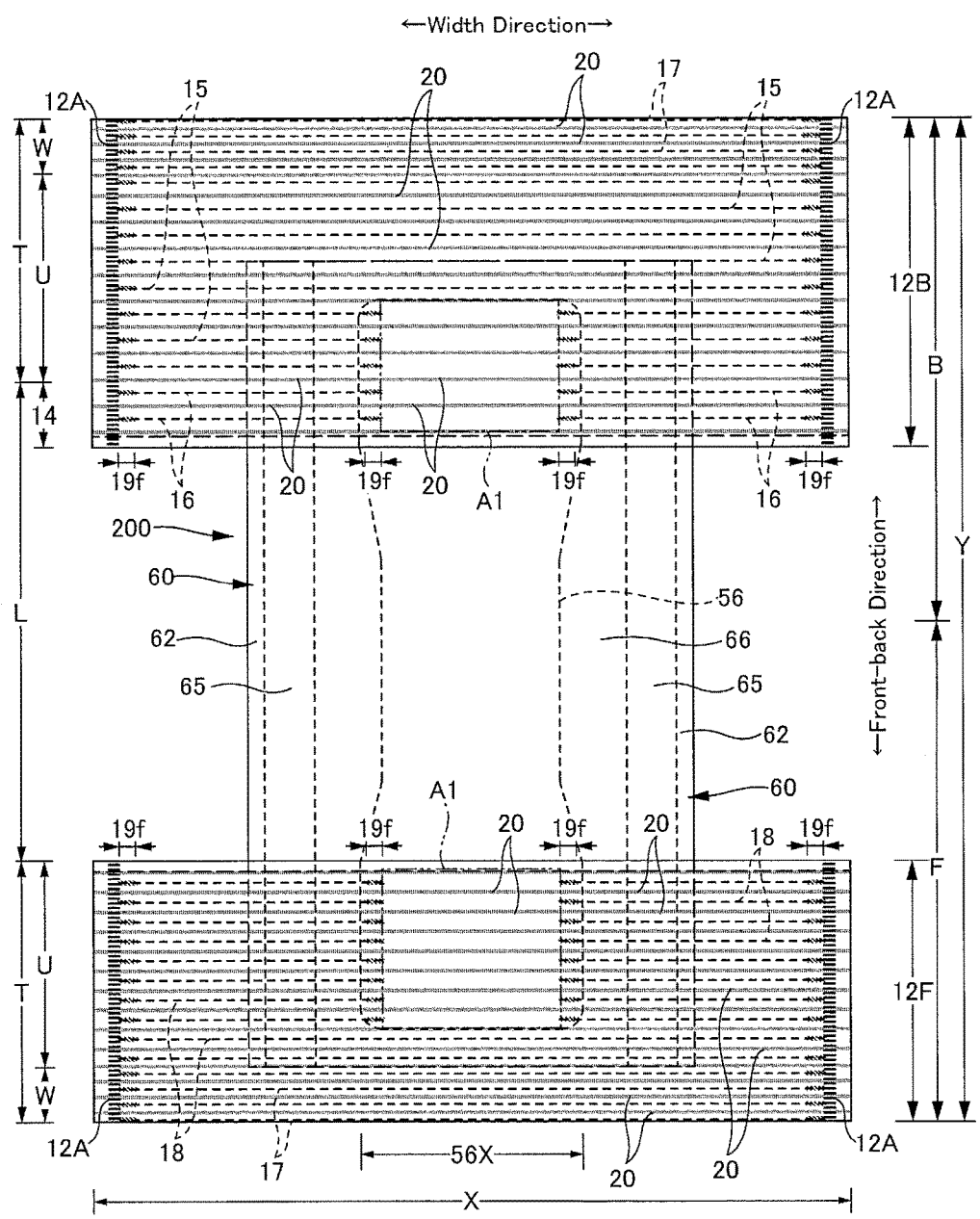
FIG. 2 is a plan view of the external face of the underpants-type disposable diaper in an unfolded state.
Figure 11:
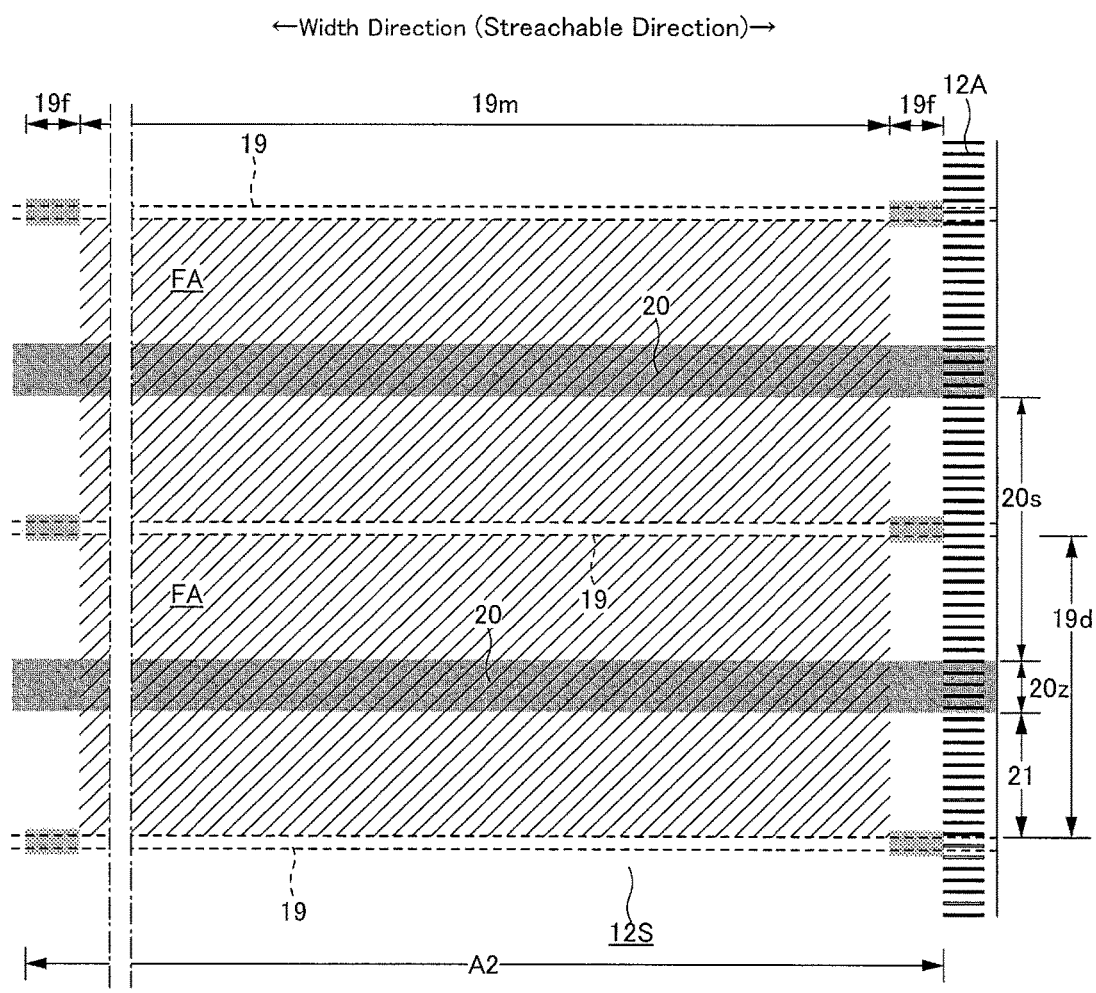
FIG. 11 is an enlarged plan view of essential components of the outer member in an unfolded state.
Figure 16:
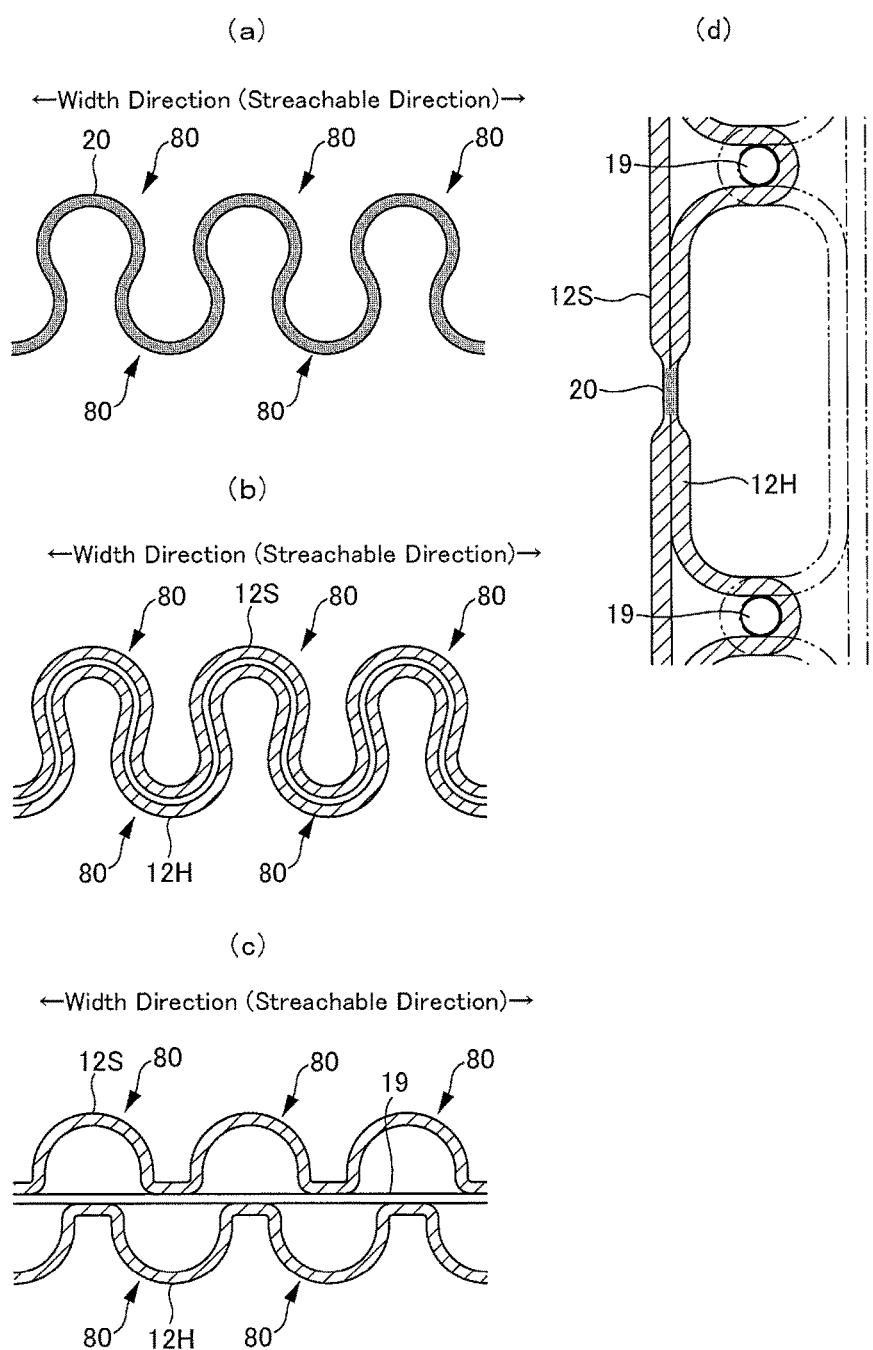
FIG. 16(a) is a cross-sectional view of the outer member taken along line 8-8 in an unstretched state.
FIG. 16(b) is a cross-sectional view of the outer member taken along line 9-9 in an unstretched state.
FIG. 16(c) is a cross-sectional view of the outer member taken along line 10-10 in an unstretched state.
FIG. 16(d) is a cross-sectional view of the outer member taken along line 7-7 in an unstretched state.

With reference to FIGS. 2, 5, and 11, inter-free regions FA defined between the free sections 19m of the resilient and elastic members 19 adjacent to each other in the front-back direction (the hatched areas in FIG. 11, which are omitted in other drawings) include the sheet bonding sections 20 formed by bonding the outer sheet layer 12S and the inner sheet layer 12H. In a completely unfolded state, the two sheet layers 12S and 12H are flat without corrugations. In a contracted state of the outer members 12S and 12H due to contraction of the resilient and elastic members 19, such as the unstretched state, the two sheet layers 12S and 12H conform with each other in a wave pattern to form corrugations 80 on the front and back faces thereof, as illustrated in FIG. 16. The portion indicated by the dash-double dot lines in FIG. 16(d) are the corrugations 80 disposed in an opposite direction adjacent to the corrugations 80 indicated by the solid lines.

Figure 15:
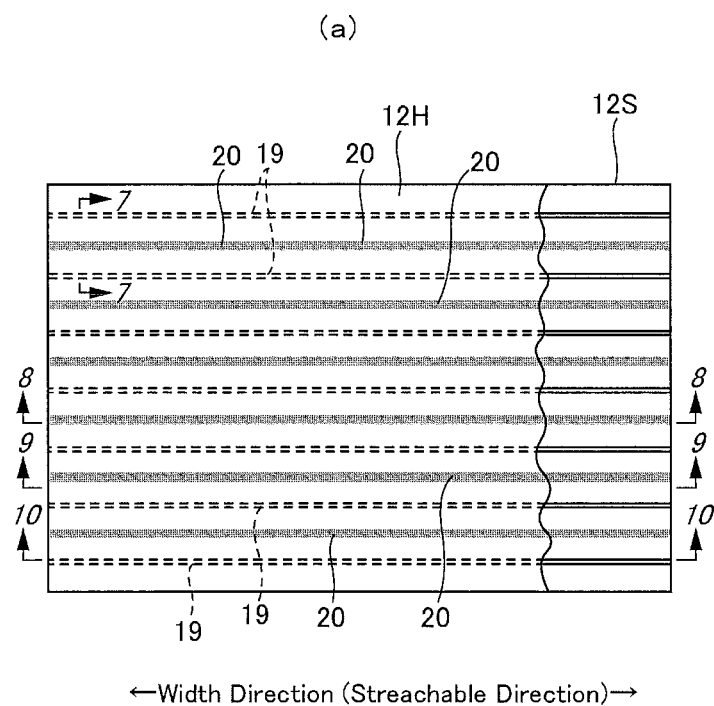
FIG. 15(a) is an enlarged plan view of essential components of the outer member in an unfolded state.
FIG. 15(b) is a cross-sectional view of the outer member taken along line 7-7 in an unfolded state.
Figure 15:
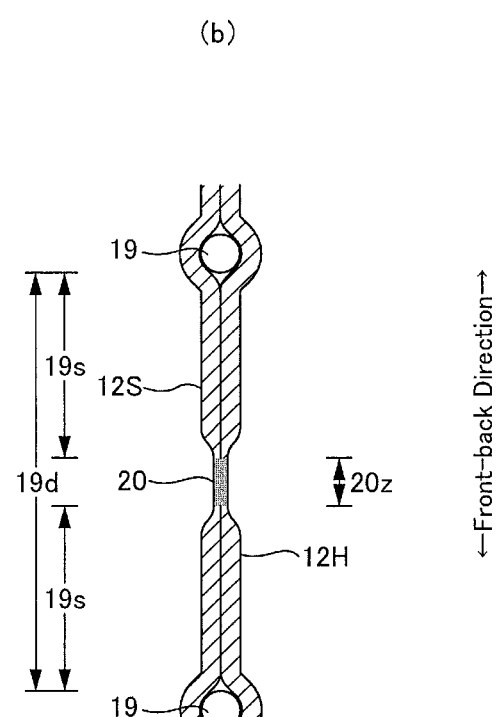

With reference to FIGS. 15 and 16, the sheet bonding sections 20 are formed through welding of the outer sheet layer 12S and the inner sheet layer 12H by ultrasonic sealing or heat sealing. Alternatively, the sheet bonding sections 20 may be formed through bonding of the outer sheet layer 12S and the inner sheet layer 12H with a hot-melt adhesive. Formation of the sheet bonding sections 20 through welding is advantageous in that complicated patterns can be readily formed (so that registration of the design may be possible) but is disadvantageous in that the sheets may readily tear along the sheet bonding sections 20. Formation of the sheet bonding sections 20 with a hot-melt adhesive prevents tearing but may cause discomfort due to the hot-melt resin being sensed as a foreign material.

For the two sheet layers 12S and 12H conforming with each other in a wave pattern as illustrated in FIG. 16, the tops of the corrugations 80 can curve more gradually than those of the traditional art because of increased stiffness simply due to the number of sheet layers and the difference in the curvature of the two sheet layers 12S and 12H (the difference is particularly significant in a unstretched state). This causes a smooth hand feel and ready compression in the thickness direction, to enhance the softness of the texture. Moreover, in the two sheet layers 12S and 12H conforming with each other in a gentle wave pattern, the distance increases between adjacent peaks and adjacent troughs of the wave pattern in the stretchable direction. This reduces the effect of the adjacent peaks and the adjacent troughs respectively supporting each other when the wave pattern is compressed or distorted in the thickness direction. This also is presumed to contribute to a softer texture. This is also apparent through a comparison of the stretchable structure of the conventional sample depicted in the area defined by the dash-double dot lines in FIG. 18(a) and the stretchable structure of the sample according to the present invention in the area defined by the dash-double dot lines in FIG. 18(b). The stretchable structure of the conventional sample in the area defined by the dash-double dot lines is the same as that illustrated in FIG. 17.

In the case where the front and back faces of a smooth material are pinched between fingers, a double layered material feels smoother than a single layered material, even if the material is the same. This is because the frictional resistance between the fingers or between a finger and the material is smaller than the frictional resistance between the layers of the material, and thus low frictional resistance (smoothness) is sensed when a double layered material is pinched. Two sheet layers conforming to each other are presumed to enhance the sense of smoothness. Thus, the preferred frictional characteristics of the sheet material for the two sheet layers 12S and 12H are as described above.

The length 20z in the front-back direction of the sheet bonding sections 20 in each inter-free region FA may be within the range of 5% to 100% of the front-back interval 19d of adjacent fixed ends 19f in the front-back direction (i.e., the front-back intervals of the resilient and elastic members 19), preferably 5% to 50%. This corresponds to a specific length preferably within the range of 0.5 to 10 mm.

In an unfolded state of the intermittent stretchable regions A2 and A3, it is preferred that unbonded regions 21 free from the sheet bonding sections 20 are continuously disposed in the width direction on the two sides of the respective inter-free regions FA in the front-back direction, to allow free shift of the free sections 19m of the resilient and elastic members 19 in the front-back direction (the direction orthogonal to the stretchable direction) within the areas between the sheet bonding sections 20, thereby providing a stretchable structure with excellent fit. In specific, the resilient and elastic members 19 and the sheet bonding sections 20 in an unfolded state are disposed over the entire width, apart from each other in the front-back direction, as illustrated in FIGS. 11 to 14. Since the resilient and elastic members 19 are shiftable in the front-back direction in the areas between adjacent sheet bonding sections 20, the intermediate portions of the resilient and elastic members 19 may shift in the front-back direction after the diaper is worn in a normal state or in an unstretched state and come into contact with the sheet bonding sections 20. The front-back length of the unbonded regions 21 may be appropriately determined. This length may be within the range of 10% to 49% of the front-back interval 19$d$ of the fixed ends 19$f$ adjacent in the front-back direction, preferably 25% to 49%. This corresponds to a specific length within the range of 2 to 12 mm, preferably 4 to 9 mm.

The sheet bonding sections 20 may have any wave pattern on the two sheet layers 12S and 12H conforming to each other in a contracted state. For the two sheet layers 12S and 12H to maintain a wave pattern while conforming to each other in a contracted state, the unity of the sheet layers 12S and 12H should be maintained at a certain level. For example, as in the traditional art illustrated FIG. 17, in the case that the areas free from the sheet bonding sections 20 are continuously aligned in the direction orthogonal to the stretchable direction (back-front direction in the drawings), the two sheet layers 12S and 12H expand and move apart from each other in the areas free from the sheet bonding sections 20. In contrast, the two sheet layers 12S and 12H in an integrated body inevitably conform to each other in a wave pattern.

From such a view point, the sheet bonding sections 20 in a preferred pattern are substantially continuously in the width direction to form a continuous line or continuous strip, as illustrated in FIGS. 11 to 14 and 21 to 23. The area in which the sheet bonding sections 20 may be substantially continuous in the width direction may extend over the entire width of the outer members 12F and 12B. Alternatively, the sheet bonding sections 20 may be partially or entirely absent in areas other than the inter-free regions FA.

The intermittent stretchable regions A2 and A3 of the outer members 12F and 12B having such configurations include the sheet bonding sections 20 substantially continuous in the stretchable direction. Thus, the two sheet layers 12S and 12H in an unstretched state only deform in such a manner that the two sheet layers conform to each other, as illustrated in FIG. 16. As a result, the two sheet layers 12S and 12H in a contracted state, including an unstretched state, due to contraction of the resilient and elastic members 19 form a wave pattern in which the two sheet layers 12S and 12H conform to each other, thereby forming the corrugations 80 on the front and back faces.

Figure 22:
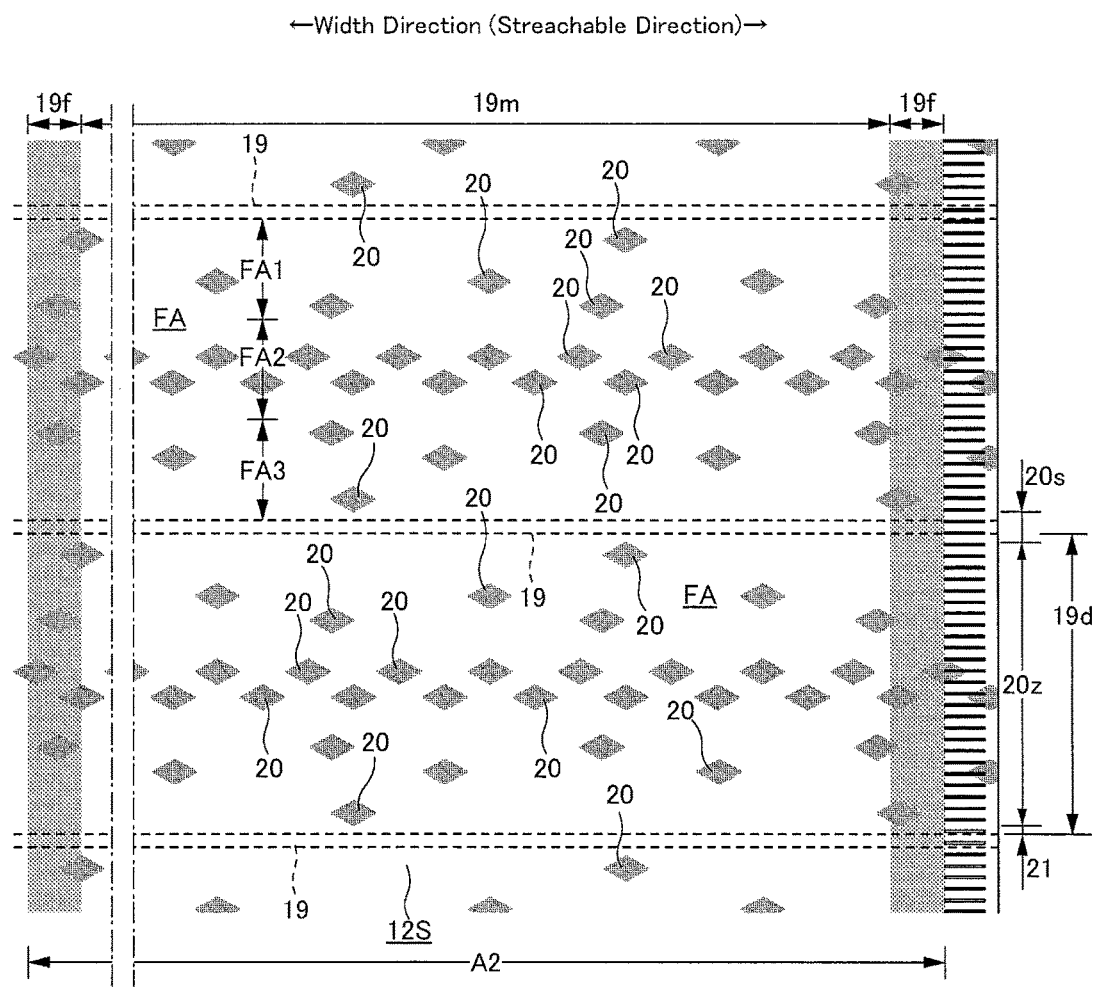
FIG. 22 is an enlarged plan view of essential components of the outer member in an unfolded state.
Figure 23:
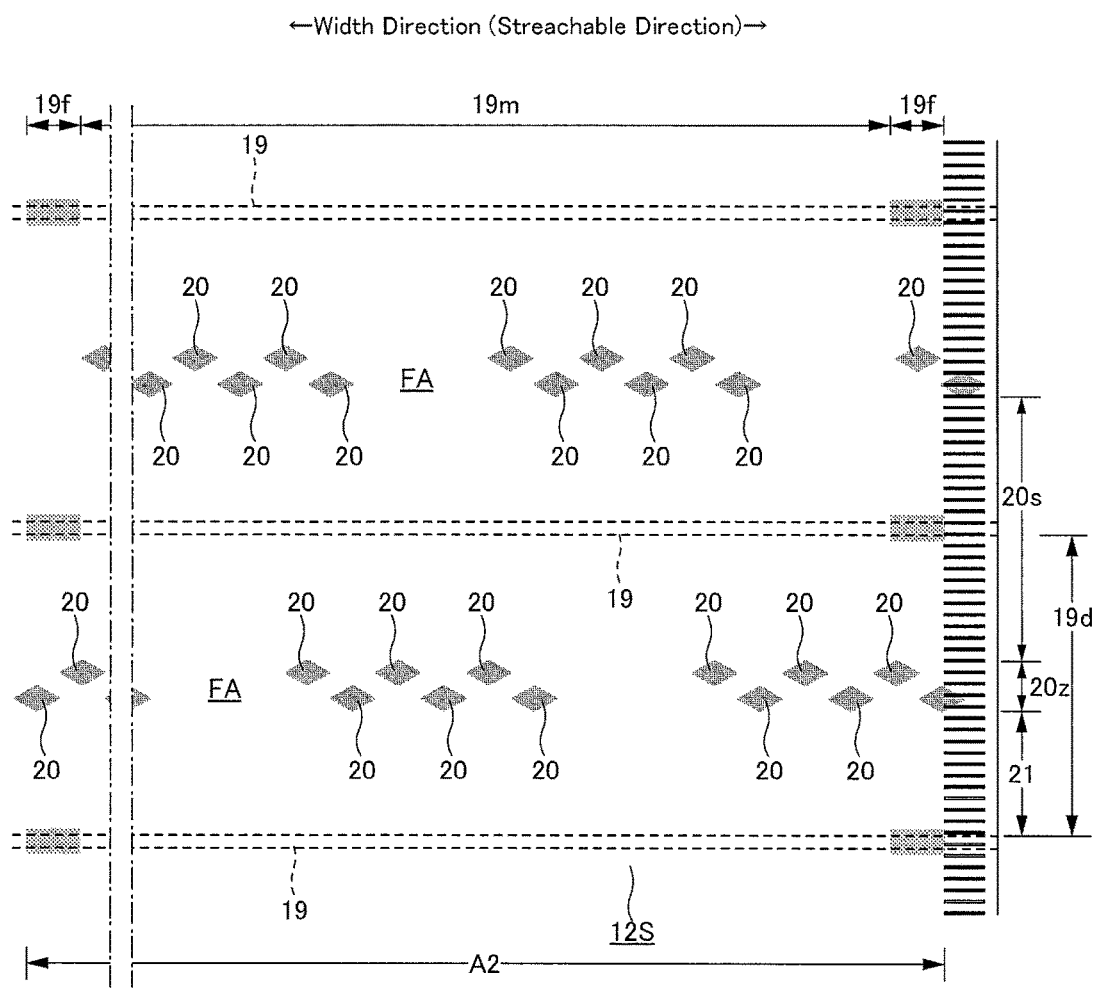
FIG. 23 is an enlarged plan view of essential components of the outer member in an unfolded state.

Examples of the configurations in which the sheet bonding sections 20 substantially continuously extend in the width direction include a configuration in which the sheet bonding sections 20 continuously extend in the width direction (the two sheet layers 12S and 12H are bonded at continuous lines in the width direction) as illustrated in FIGS. 11 and 12; a configuration in which the sheet bonding sections 20 are disposed intermittently in the width direction (the two sheet layers 12S and 12H are intermittently bonded in the width direction) but a partial or entire group of the multiple sheet bonding sections 20 disposed in a single inter-free region FA is continuous (without interruption) along the front-back direction as illustrated in FIGS. 13, 14, 21, and 22; and a configuration in which a partial or entire group of the multiple sheet bonding sections 20 disposed in two adjacent inter-free regions FA in the front-back direction is continuous (without interruption) along the front-back direction as illustrated in FIG. 23.

The sheet bonding sections 20 may be completely continuous in the stretchable direction, but in such a case, a reduction in softness is inevitable. Fusion of the sheet layers composed of non-woven fabric or the like at the sheet bonding sections 20 in the form of continuous lines causes ready tearing of the sheets along the sheet bonding sections 20. Thus, it is preferred to intermittently dispose the sheet bonding sections 20 along the stretchable direction.

Figure 25:
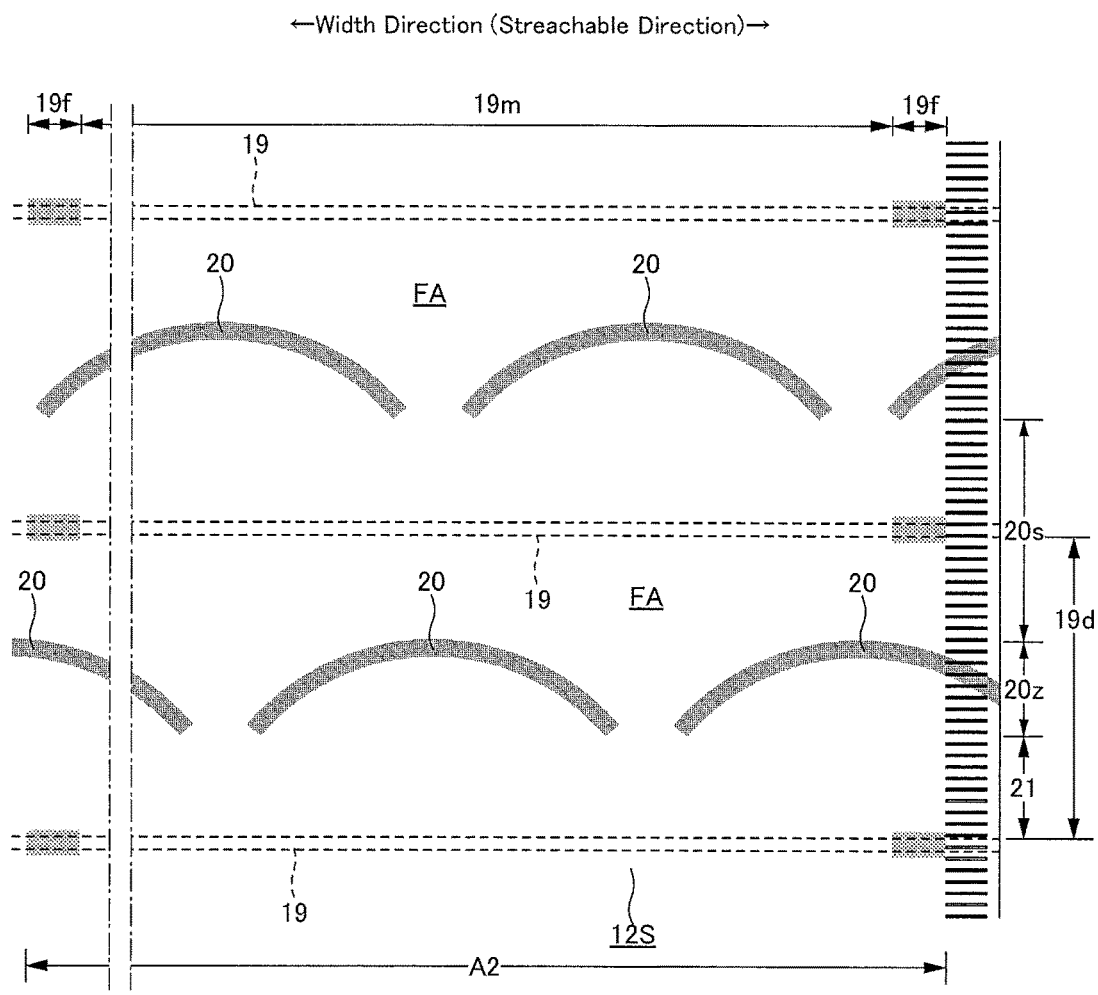
FIG. 25 is an enlarged plan view of essential components of the outer member in an unfolded state.
Figure 26:
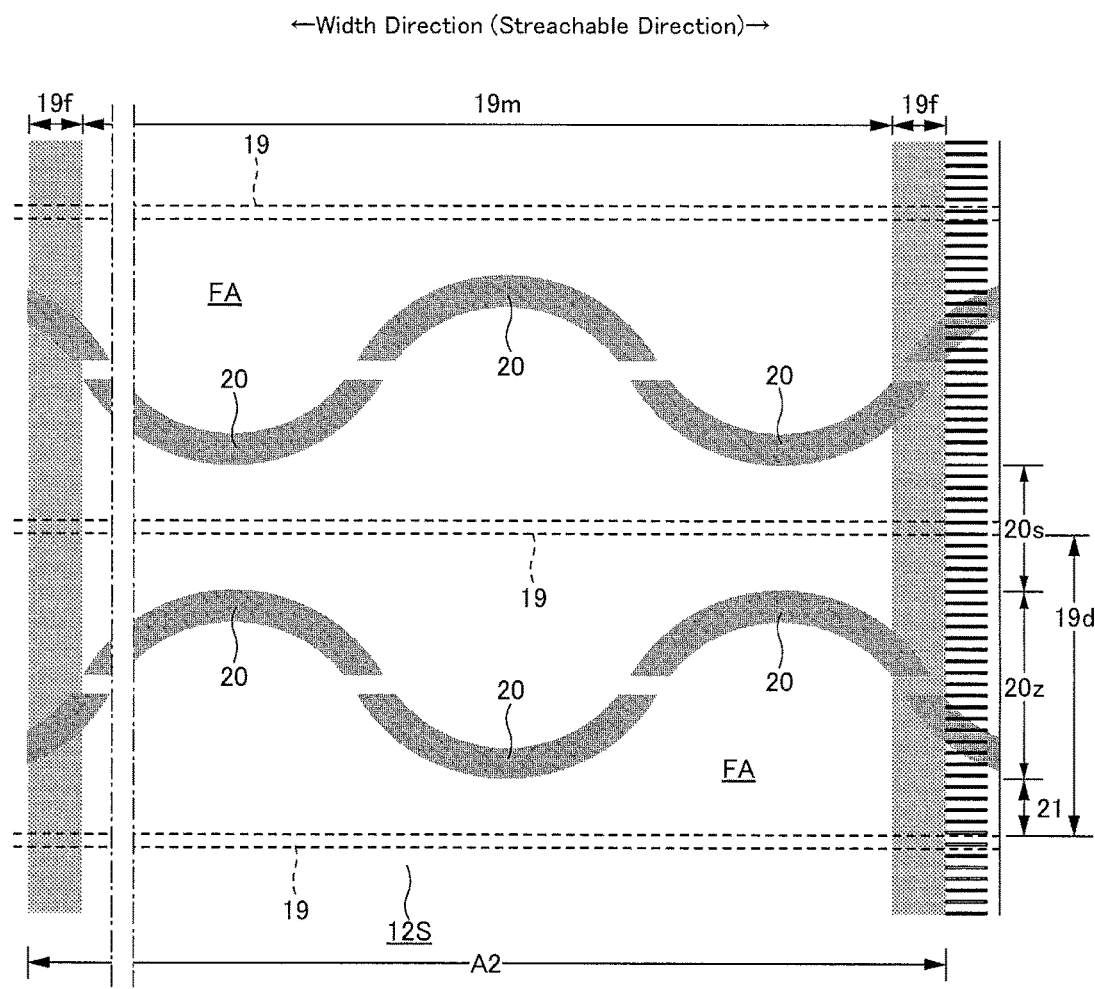
FIG. 26 is an enlarged plan view of essential components of the outer member in an unfolded state.
Figure 27:
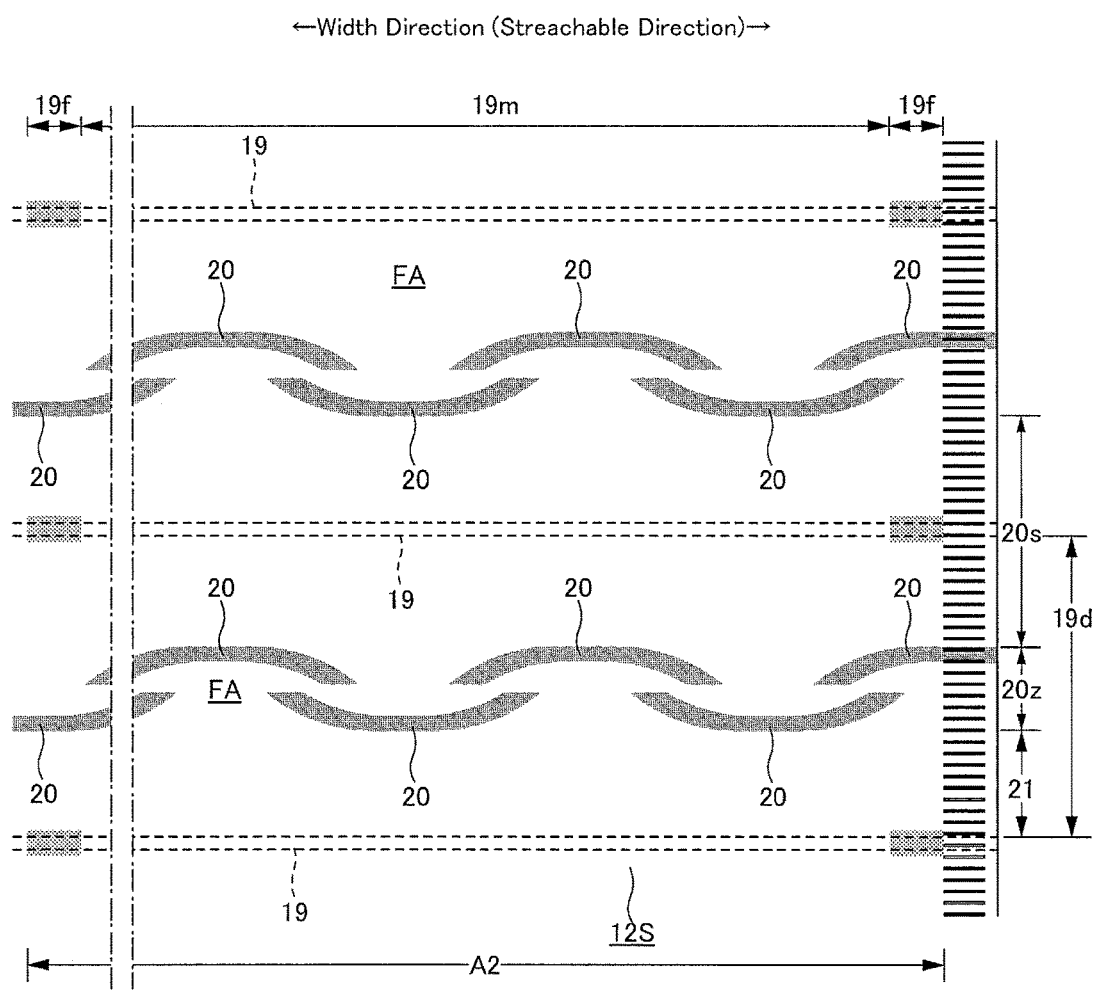
FIG. 27 is an enlarged plan view of essential components of the outer member in an unfolded state.

Configurations in which the sheet bonding sections 20 are intermittently disposed but is substantially continuous along the width direction include a single-array configuration in which the sheet bonding sections 20 align at predetermined intervals in a single array along the stretchable direction as illustrated in FIG. 13; and a multi-array configuration in which multiple arrays of sheet bonding sections 20 are disposed in the front-back direction, and the sheet bonding sections 20 in each array are disposed in a staggered pattern such that they overlap with the sheet bonding sections 20 in the other arrays adjacent in the front-back direction as illustrated in FIGS. 14, 19 to 21, 26, and 27. It is preferred to intermittently dispose the sheet bonding sections 20 in the width direction in this way because softness is less likely to decrease. The individual sheet bonding sections 20 in the multi-array configuration are smaller than those in the single-array configuration, and thus the softness is more enhanced in the multi-array configuration. Moreover, the two sheet layers 12S and 12H bonded at multiple sheet bonding sections 20 have a sufficient bonding strength. As illustrated in FIGS. 23 and 25, the groups of sheet bonding sections 20 in the respective inter-free regions FA are not substantially continuous in the width direction in the individual groups but are substantially continuous in the width direction when multiple groups of the sheet bonding sections 20 in the inter-free regions FA adjacent to each other in the front-back direction are collectively viewed. This configuration achieves the most enhanced softness.

In the single-array configuration, it is preferred that the width-direction overlapping width 20$w$ of a first sheet bonding section 20 and a second adjacent sheet bonding section 20 in the stretchable direction be larger than the front-back interval 20$d$ (the maximum value is selected, if the interval varies) of the first sheet bonding section 20 and the second sheet bonding section 20 in the overlapping area. In the multi-array configuration, it is preferred that the width-direction overlapping width of a first sheet bonding section 20 in an array and a second sheet bonding section 20 in another array adjacent in the front-back direction be larger than the front-back interval of these sheet bonding sections 20.

Figure 14:
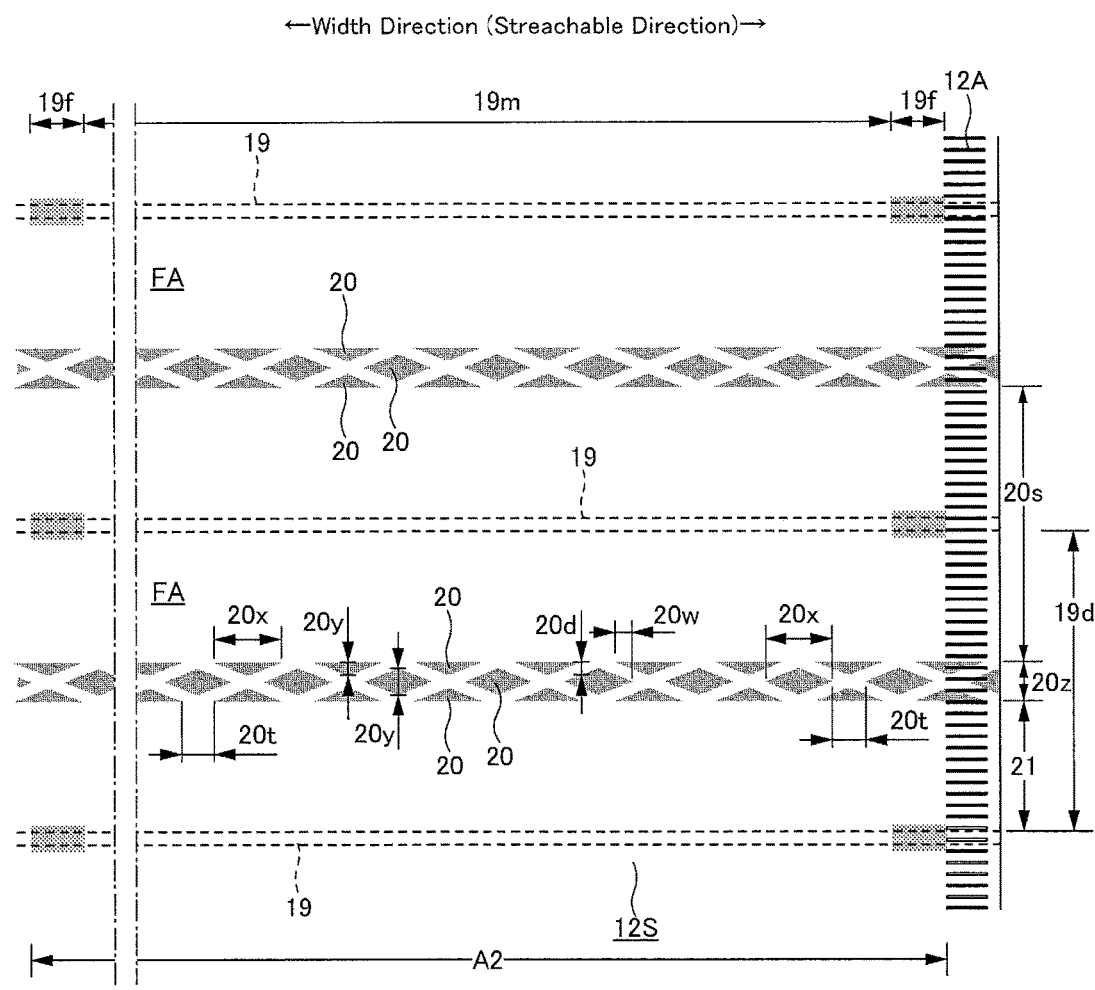
FIG. 14 is an enlarged plan view of essential components of the outer member in an unfolded state.

In the multi-array configuration, in particular, it is preferred that the sheet bonding sections 20 in the respective arrays be disposed such that portions of the sheet bonding sections 20 in the front-back direction in the respective arrays and portions of the sheet bonding sections 20 in the front-back direction in adjacent arrays overlap in the front-back direction, as illustrated in FIG. 14.

The individual sheet bonding sections 20 may have any appropriate shape, such as a circle, an ellipse, or a polygon (triangle, square, etc.). To simplify the shape of the sheet bonding sections 20 in a single-array configuration, triangles, parallelograms (as illustrated in the drawings), and combination thereof are preferred. To simplify the shape of the sheet bonding sections 20 in a multi-array configuration, triangles, diamonds, and combination thereof (as illustrated in the drawings) are preferred.

Besides such punctate sheet bonding sections 20, the sheet bonding sections 20 may have linear shapes extending in the width direction, as illustrated in FIGS. 25 to 28. In the configuration illustrated in FIG. 25, the sheet bonding sections 20 are disposed at predetermined intervals in the width direction, the sheet bonding sections 20 having an arcuate shape with a central angle of 180 degrees or less or a similar curved shape. In the configuration illustrated in FIG. 26, the sheet bonding sections 20 are aligned in the with direction in a sinusoidal or similar wave pattern, the sheet bonding sections 20 having an arcuate shape with a central angle of 180 degrees or less or a similar curved shape. In the configuration illustrated in FIG. 27, the sheet bonding sections 20 are disposed in an alternating pattern in two arrays in the width direction, the sheet bonding sections 20 having an arcuate shape with a central angle of 180 degrees or less or a similar curved shape. In the configuration illustrated in FIG. 28, the linear sheet bonding sections 20 are arrayed in a staggered pattern in the width direction.

Figure 24:
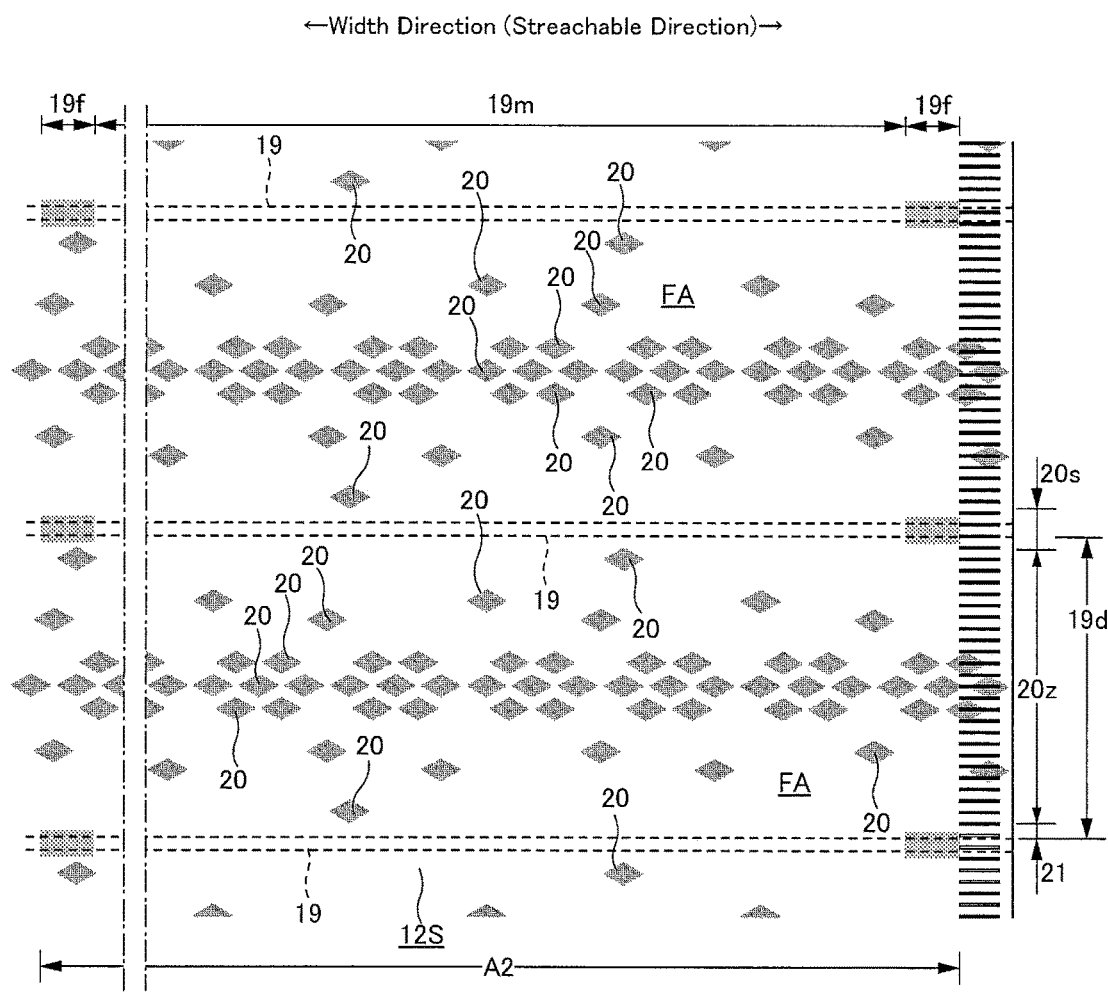
FIG. 24 is an enlarged plan view of essential components of the outer member in an unfolded state.
Figure 28:
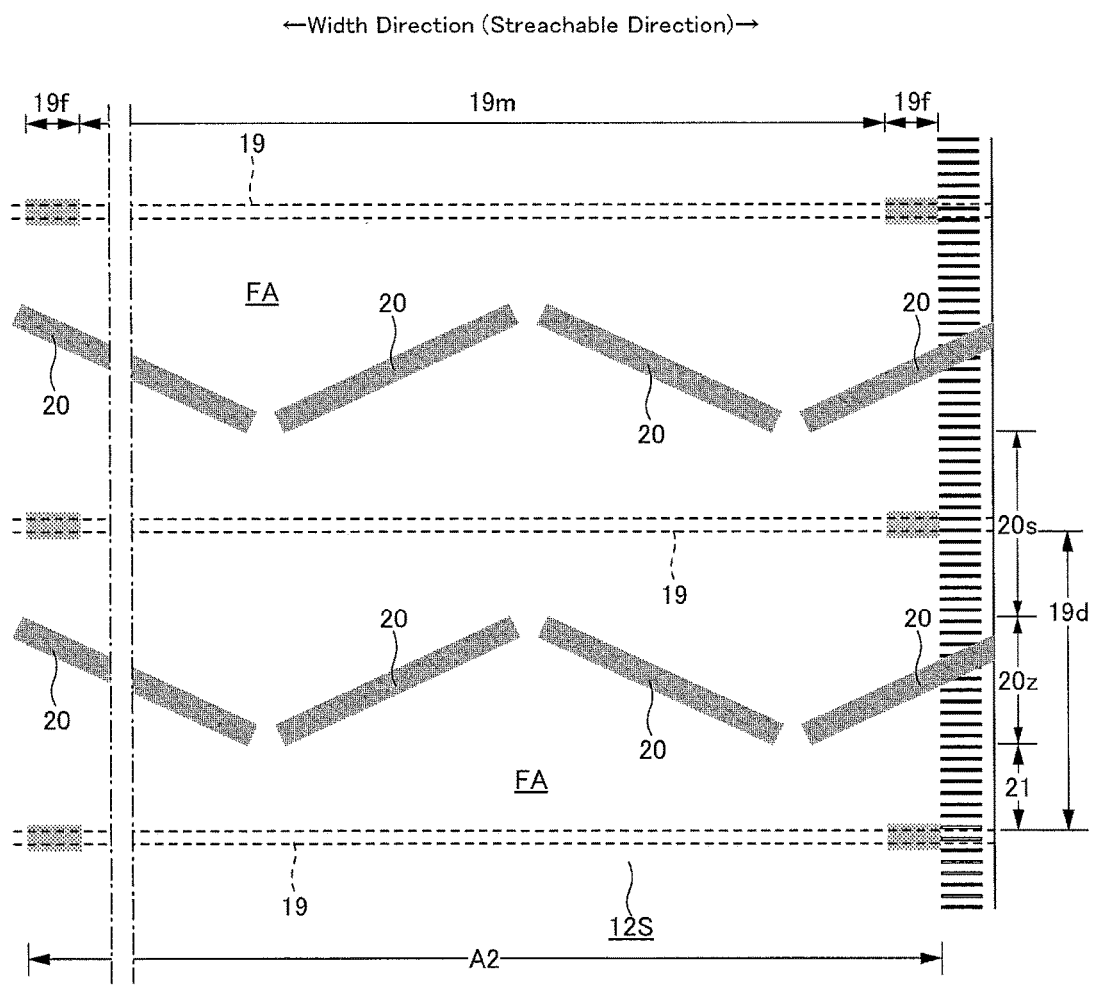
FIG. 28 is an enlarged plan view of essential components of the outer member in an unfolded state.

The sheet bonding sections 20 may have any appropriate dimensions and may be arrayed at any appropriate intervals. Sheet bonding sections 20 intermittently disposed preferably have the following dimensions and intervals:

Maximum length 20x of the sheet bonding sections in the width direction: 0.5 to 5.0 mm Maximum length 20y of the sheet bonding sections in the front-back direction: 0.2 to 2.0 mm Width-direction interval 20t of the sheet bonding sections: 0.1 to 0.9 times the maximum length 20x of the sheet bonding sections in the width direction Front-back interval 20d of the sheet bonding sections: 0.5 to 1.5 times the maximum length 20y of the sheet bonding sections in the front-back direction Width-direction overlapping width 20w of the sheet bonding sections: 0.2 time or more the front-back interval 20d of the sheet bonding sections Front-back length 20z of an area of the inter-free region including the sheet bonding sections: 1 to 10 mm Front-back interval 20s of the sheet bonding sections in an adjacent inter-free region: 4 to 20 mm Alternatively, the sheet bonding sections 20 may be intermittently arrayed (substantially discontinuous) in the width direction on view of a group of sheet bonding sections 20 in each inter-free regions FA or a group of sheet bonding sections 20 in an inter-free region FA adjacent to other inter-free region FA, as illustrated in FIGS. 24 and 28. That is, the high overall unity of the two sheet layers 12S and 12H can be achieved even with this configuration by forming a sufficiently small area in which the sheet bonding sections 20 are discontinuous in the width direction and sufficiently long areas in which the sheet bonding sections 20 are substantially continuous in the width direction, disposed on both sides of the sufficiently small area. Thus, in the former area, the two sheet layers 12S and 12H deform to maintain continuity with the latter areas so that the two sheet layers 12S and 12H form a wave pattern while conforming to each other, as in the configuration illustrated in FIG. 16.

The two sheet layers 12S and 12H in the inter-free regions FA have an increased flexibility toward the central area in the front-back direction. Thus, it is preferred to increase the area rate of the sheet bonding sections 20 to enhance the unity of the two sheet layers 12S and 12H because the conforming state of the two sheet layers 12S and 12H is barely distorted. At the edges of the inter-free regions FA in the front-back direction (i.e., in the vicinity of the resilient and elastic members 19), the resilient and elastic members 19 hinder the approximation of the two sheet layers 12S and 12H. Thus, for the sheet layers 12S and 12H to absorb the hindering effect of the resilient and elastic members 19 and independently deform (contract or bend) so that the sheet layers 12S and 12H conform with each other, it is preferred that the area rate of the sheet bonding sections 20 be small and the flexibility of the sheet layers 12S and 12H to be high. Low flexibility of the sheet layers 12S and 12H relative to the resilient and elastic members 19 causes the resilient and elastic members 19 and the sheet layers 12S and 12H to deform as an integrated body. Thus, the sheet layers 12S and 12H slightly separate from the resilient and elastic members 19 and form many small wrinkles, which generate a coarse unpleasant texture. Thus, a preferred configuration includes sheet bonding sections 20 arrayed such that the area rate of the sheet bonding sections 20 (the rate of the areas of the sheet bonding sections 20 per unit area) gradually decreases toward the two front-back sides in each inter-free region FA, as illustrated in the drawings.

The area rate of the sheet bonding sections 20 can be varied toward the two front-back sides of each inter-free region FA by providing unbonded regions 21, as illustrated in the drawings, and/or providing a smaller number of sheet bonding sections 20 in arrays closer to the front-back sides of the inter-free regions FA in a multi-array configuration. The shape and/or area of the individual sheet bonding sections 20 may be modified.

In an unfolded state of the intermittent stretchable regions A2 and A3, each inter-free region FA includes three portions FA1, FA2, and FA3 having equal widths in the front-back direction, where the central portion FA2 is positioned in the center of the portions FA1, FA2, and FA3 in the front-back direction and the side portions FA1 and FA3 are positioned on the two sides of the central section FA2 (see FIG. 22). Usually, it is preferred that the area rate of the sheet bonding sections 20 to the central portions FA2 be within the range of 3% to 25%, preferably 5% to 20%, and the area rate of the sheet bonding sections 20 to the respective side portions FA1 and FA3 be 10% or less, preferably 3% or less. The rate of the area rate of the sheet bonding sections 20 to the central portions FA2 to the area rate of the sheet bonding sections 20 to the respective side portions FA1 and FA3 is 20% or less, preferably 10% or less. It is even more preferred that the side portions FA3 is free from the sheet bonding sections 20 because this increases not only the flexibility of the sheet layers 12S and 12H relative to the resilient and elastic members 19 but also decreases the risk of the sheet bonding sections 20 coming into contact with the resilient and elastic members 19 during production (the risk of the resilient and elastic members 19 unintentionally being cut in the case of bonding by welding).

Other configurations may include a configuration in which the area rate of the sheet bonding sections 20 is constant across the inter-free regions FA in the front-back direction and a configuration in which the area rate of the sheet bonding sections 20 gradually increases toward the two front-back sides of each inter-free region FA.

(Formation of Non-Stretchable Region)

The non-stretchable region A1 can be formed by disposing the resilient and elastic members 19 between the inner sheet layer 12H and the outer sheet layer 12S; fixing only the fixed ends 19f of the resilient and elastic members 19 with a hot-melt adhesive at the edge portions in areas to be defined as the intermittent stretchable regions A2; and then cutting each resilient and elastic member 19 at one or more intermediate positions in the width direction within the areas to be the non-stretchable region A1 through pressurization or heating, or snicking substantially all of the resilient and elastic members 15, 16, and 19, so that the elasticity of the intermittent stretchable regions A2 is preserved while the elasticity of the non-stretchable region A1 is nullified.

FIG. 19(a) illustrates a case where the resilient and elastic members 19 are cut at one intermediate position in the width direction. The cutting is performed with a seal roll 70 having a circumferential surface provided with press segments 71 each including a cutting convex 72 disposed at a given position on the circumference and heated to a predetermined temperature; and an anvil roll 80 having a smooth surface and facing the seal roll 70. The target to be cut, which includes the inner sheet layer 12H, the outer sheet layer 12S, and the resilient and elastic members 19 disposed therebetween, is disposed between the rolls 70 and 80, and only the resilient and elastic members 19 in the portions nipped between the cutting convexes 72 and the circumferential surface of the anvil roll 80 are cut through pressurization or heating. In a product processed in this way, each non-stretchable region A1 includes residual resilient and elastic members 18 containing only the residual pieces continuing from the resilient and elastic members 19 in the intermittent stretchable regions A2, and one melted mark 22 or cutting mark between the outer sheet layer 12S and the inner sheet layer 12H, as illustrated in FIGS. 20(a) and 20(b). Although not illustrated, in the case of cutting at multiple positions, a seal roll 70 having multiple cutting convexes 72 along the circumference may be used.

FIG. 19(b) illustrates a case where the resilient and elastic members 19 are substantially entirely snicked. The snicking is performed with a seal roll 70 having a circumferential surface provided with press segments 71 each including multiple cutting convexes 72 intermittently disposed in a staggered pattern and an anvil roll 80 having a smooth surface facing the seal roll 70. The target to be cut, which includes the inner sheet layer 12H, the outer sheet layer 12S, and the resilient and elastic members 15, 16, 17 and 19 disposed therebetween, is disposed between the rolls 70 and 80, and only the resilient and elastic members 19 in the portions nipped between the cutting convexes 73 and the circumferential surface of the anvil roll 80 are cut by press or heat. In a product processed this way, the non-stretchable region A1 includes residual resilient and elastic members 18 intermittent in the front-back and width directions containing residual pieces continuing from the resilient and elastic members 19 in the stretchable regions A2 and cut pieces of the resilient and elastic members discontinued from the resilient and elastic members 19 in the intermittent stretchable regions A2, between the outer sheet layer 12S and the inner sheet layer 12H; and melted marks 22 or cutting marks, as illustrated in FIG. 20(c), (Sheet Bonding Sections in Non-Stretchable Regions)

Figure 6:
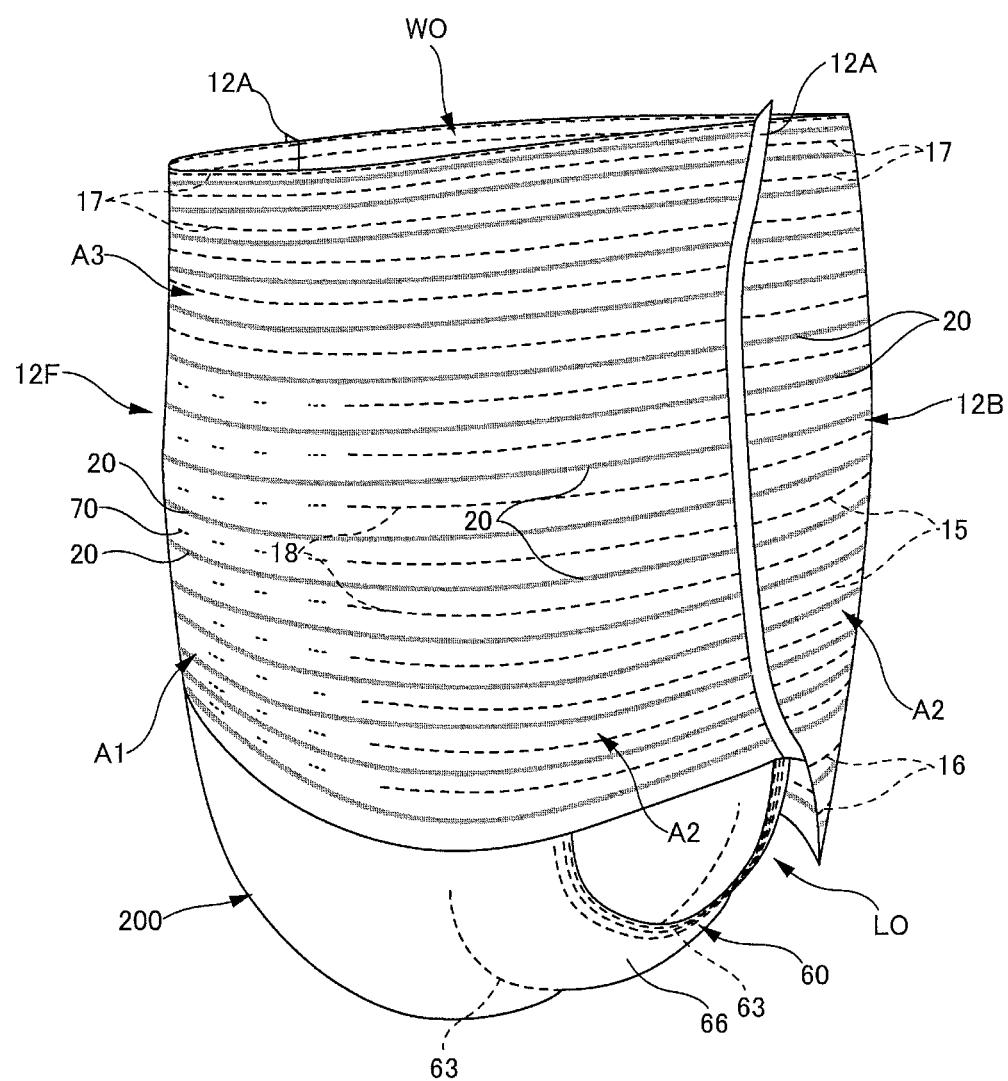
FIG. 6 is a perspective view of an underpants-type disposable diaper.

Although the sheet bonding sections 20 may be omitted in the non-stretchable region A1, the sheet bonding sections 20 should preferably be provided to prevent the outer sheet layer 12S from being undesirably displaced or separated from the inner sheet layer 12H. The sheet bonding sections 20 may be of any type as long as the two sheet layers 12S and 12H are bonded. In the non-stretchable region A1, as illustrated in FIGS. 2, 6, and 20, it is preferred that the residual resilient and elastic members 70 be unfixed to the two sheet layers 12S and 12H and the two sheet layers 12S and 12H be bonded at the sheet bonding sections 20 substantially continuous in the width direction on the two sides of the residual resilient and elastic members 70 in the front-back direction. The residual resilient and elastic members 70 unfixed to the two sheet layers 12S and 12H in this way can completely cancel out the contraction force of the residual resilient and elastic members 70 applied to the two sheet layers 12S and 12H. In the non-stretchable region A1, the sheet bonding sections 20 substantially continuous in the width direction bond the two sheet layers 12S and 12H on the two sides of the residual resilient and elastic members 70 in the front-back direction. Thus, a shift of the residual resilient and elastic members 70 in the front-back direction is limited to the area between adjacent sheet bonding sections 20 on both sides of the residual resilient and elastic members 70 in the front-back direction. This prevents a large shift that impairs the pleasing appearance. In the non-stretchable region A1, the residual resilient and elastic members 70 may be fixed to the two sheet layers 12S and 12H with a hot-melt adhesive. In the case where the resilient and elastic members 19 are cut at one or more intermediate positions in the width direction, as illustrated in FIGS. 20(a) and 20(b), the volume of the hot-melt adhesive to be applied should be adjusted so as to reduce the adhesive force. In the case where the resilient and elastic members 19 are snicked, as illustrated in FIG. 20(c), the elasticity of the non-stretchable region A1 can be substantially nullified even with a large adhesive force.

The sheet bonding sections 20 in the non-stretchable region A1 may be basically the same as the sheet bonding sections 20 in the intermittent stretchable regions A2. Alternatively, the sheet bonding sections 20 in the non-stretchable region A1 may be different in shape, dimension, number, and position from the sheet bonding sections 20 in the intermittent stretchable regions A2. For example, multiple arrays of the sheet bonding sections 20, such as those illustrated in FIG. 13, may be disposed in the non-stretchable region A1 between the residual resilient and elastic members 70, and the distance between the residual resilient and elastic members 70 and the sheet bonding sections 20 may be narrowed to effectively prevent the shift of the residual resilient and elastic members 70. At the same time, a single array of the sheet bonding section 20 may be disposed in each intermittent stretchable region A2 between adjacent resilient and elastic members 19, as illustrated in FIG. 11, in strong consideration of the softness of the intermittent stretchable regions A2.

Figure 20:
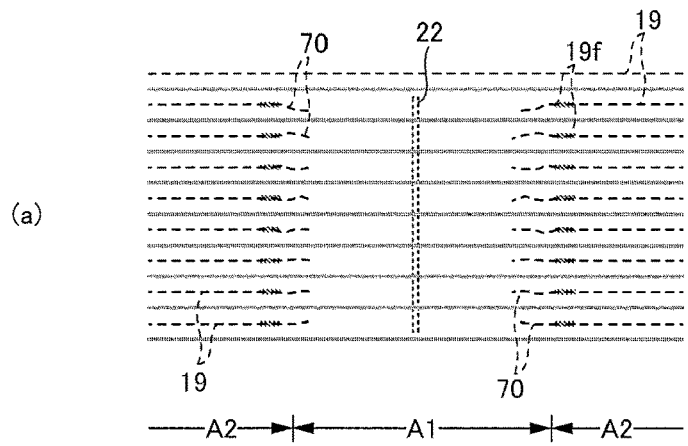
FIG. 20 is an enlarged plan view of a non-stretchable region and a stretchable region of the outer member.
Figure 20:
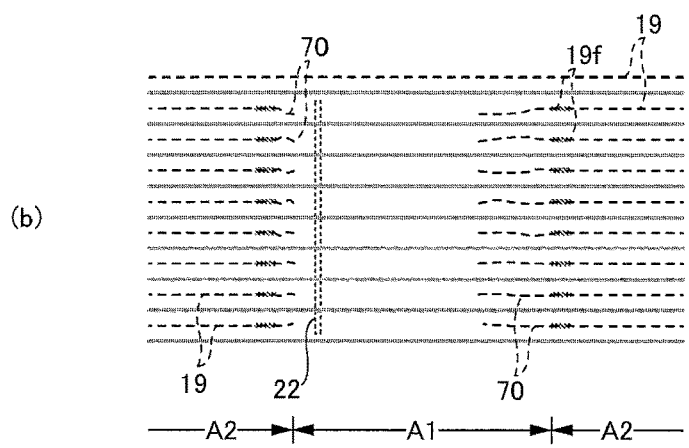
Figure 20:
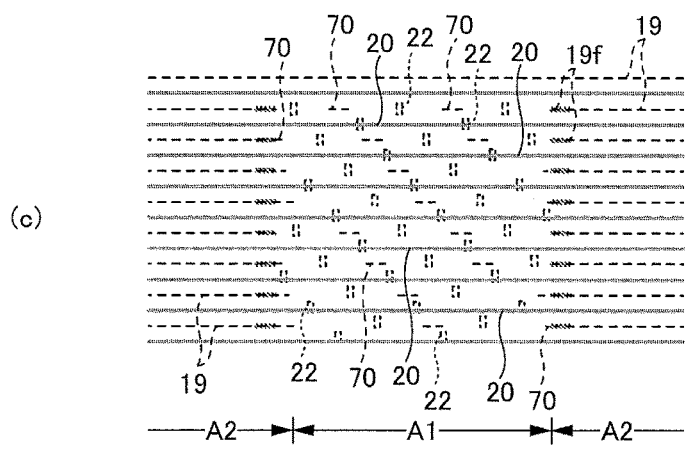
Figure 21:
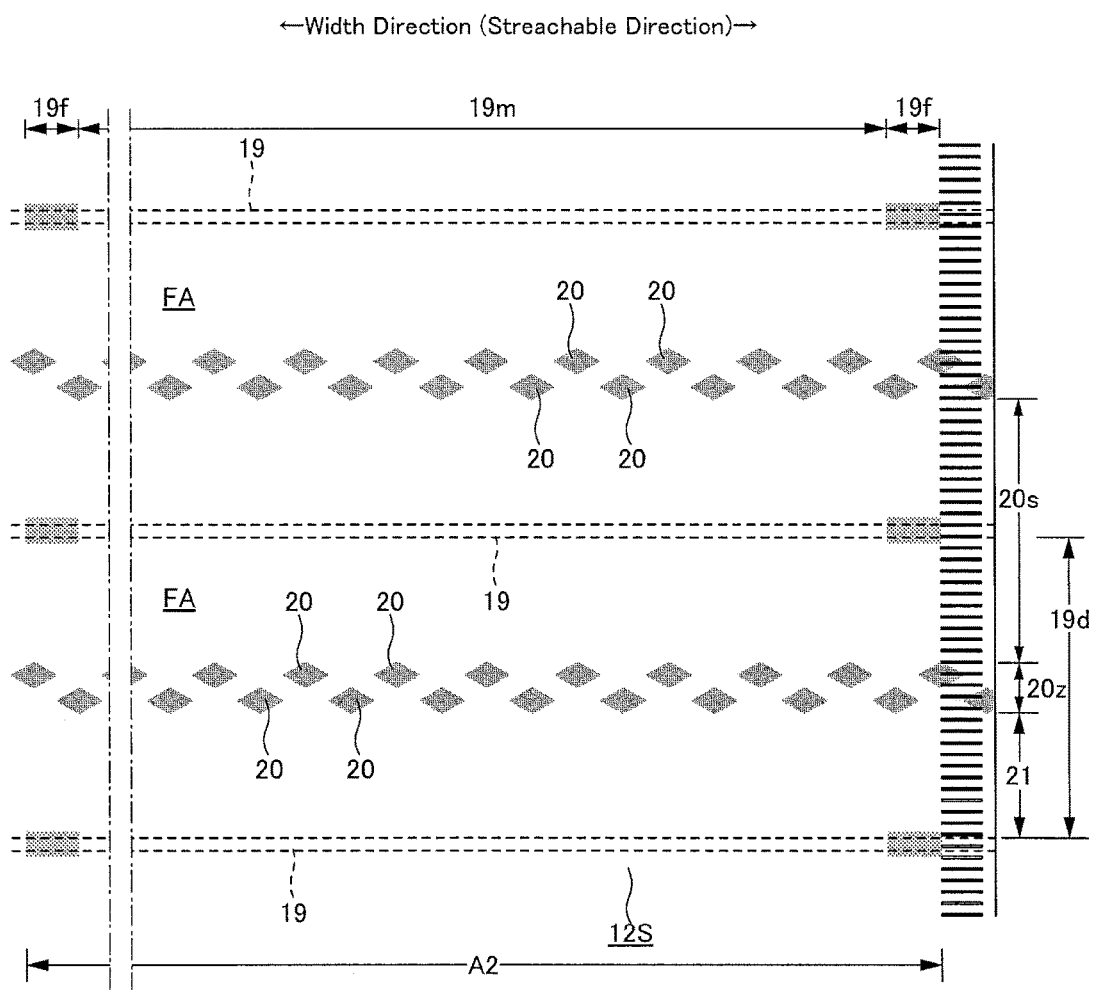
FIG. 21 is an enlarged plan view of essential components of the outer member in an unfolded state.

In view of ready and stable production, it is preferred that the sheet bonding sections 20 in the non-stretchable region A1 be identical in shape, dimension, number, and position to the sheet bonding sections 20 in the intermittent stretchable regions A2, as illustrated in FIGS. 2, 6, and 20. It is preferred that at least the sheet bonding sections 20 in the intermittent stretchable regions A2 and the sheet bonding sections 20 in the non-stretchable region A1 be substantially continuous in the width direction. The width direction of the product is the flow direction of the material during production of the outer members 12F and 12B. Thus, the sheet bonding sections 20 disposed in such a continuous pattern eliminate the need for alternation between different bonding patterns corresponding to the non-stretchable region A1 and the intermittent stretchable regions A2 at specific timings for each product. As a result, product failure due to mistiming barely occurs, and different supply components are not required in the production of products having different widths with a single production device.

In such a case, the spaces between the two sheet layers 12S and 12H in the intermittent stretchable regions A2 are in communication with the space between the two sheet layers 12S and 12H in the non-stretchable region A1. This may cause the residual resilient and elastic members 70 in the non-stretchable region A1 to shift into the space in the intermittent stretchable regions A2. Thus, as illustrated in FIGS. 13 and 14, it is also preferred to form the fixed ends 19f of the resilient and elastic members 19 in the intermittent stretchable regions A2 at at least the ends adjacent to the center in the width direction with a hot-melt adhesive that extends over the entire front-back direction of the intermittent stretchable regions A2, and to simultaneously bond the two sheet layers 12S and 12H over the entire front-back direction of the intermittent stretchable regions A2. In this way, the space between the two sheet layers 12S and 12H in the non-stretchable region A1 is sealed at the sides of the non-stretchable region A1 in the width direction, thereby preventing impairment of the pleasing appearance due to a shift of the residual resilient and elastic members 70 into the intermittent stretchable regions A2. Alternatively, an adhesive may be lightly applied to at least one of the two sheet layers 12S and 12H to only weakly bond the residual resilient and elastic members 70 to the two sheet layers 12S and 12H such that the contraction force is completely cancelled out. An increase in the frictional resistance of the two sheet layers 12S and 12H to the residual resilient and elastic members 70, in conjunction with the effect of the integrated body of the two sheet layers 12S and 12H bonded by the sheet bonding sections 20, can prevent a large shift of the residual resilient and elastic members 70. Even if an adhesive is applied to at least one of the two sheet layers 12S and 12H in this way, the residual resilient and elastic members 70 may be considered to be (substantially) unfixed to the two sheet layers 12S and 12H as long as the adhesive force is weak enough to completely cancel out the contraction force of the residual resilient and elastic members 70. In such the case, at least the fixed ends 19f of the resilient and elastic members 19 in the intermittent stretchable regions A2 adjacent to the center in the width direction do not have to be formed with the hot-melt adhesive continuous in the front-back direction of the intermittent stretchable regions A2. Thus, the volume of the adhesive to be applied can be reduced.

Other details of the sheet bonding sections 20 in the non-stretchable region A1 are omitted here because they have already been described in the section on the sheet bonding sections 20 in the stretchable regions.

(Inner Member)

The inner member 200 may have any shape and structure. For example, the inner member 200 may have the following shape and structure. The inner member 200 may have any shape. In this embodiment, the inner member 200 has a rectangular shape. The inner member 200 includes a liquid pervious top sheet 30 adjacent to the skin of the wearer, a liquid impervious sheet 11, and an absorbent element 50 disposed therebetween, as illustrated in FIGS. 3 to 5. The inner member 200 is the main section that provides an absorbing function. Reference sign 40 represents an intermediate sheet (also referred to as a second sheet) disposed between the top sheet 30 and the absorbent element 50 for quick transportation of the liquid passing through the top sheet 30 into the absorbent element 50, and reference sign 60 represents leg-surrounding gathers that extend along the edges of the absorbing face of the inner member in the width direction and erect around the legs of the wearer, to prevent leakage of excretion from the two sides of the inner member 200.

(Top Sheet)

The top sheet 30 may be composed of any liquid pervious materials, such as porous or non-porous non-woven fabric and a porous plastic sheet. In a case where the top sheet 30 also functions as a covering material of liquid impervious sheets 64 of the leg-surrounding gathers 60, as illustrated in FIGS. 3 and 4, the top sheet 30 is composed of non-woven fabric. There is no particular limitation on the kind of raw fiber for the non-woven fabric. Examples of such raw fiber include synthetic fibers based on olefin, such as polyethylene and polypropylene, polyester, and polyamide; reproduced fibers, such as rayon and cupra; natural fibers, such as cotton; and mixed fibers and composite fibers composed of two or more of these fibers. The non-woven fabric may be produced through any process. Examples of known processes include spunlacing, spunbonding, thermal bonding, melt blowing, needle punching, air through bonding, and point bonding. For example, spunbonding and spunlacing are suitable for achieving softness and draping, whereas air through bonding, point bonding, and thermal bonding are suitable for bulkiness and softness.

The top sheet 30 may be composed of a single sheet or a layered sheet formed by sticking two or more sheets to each other. Similarly, the top sheet 30 may be composed of a single sheet or two or more sheets in a planar direction.

Figure 7:
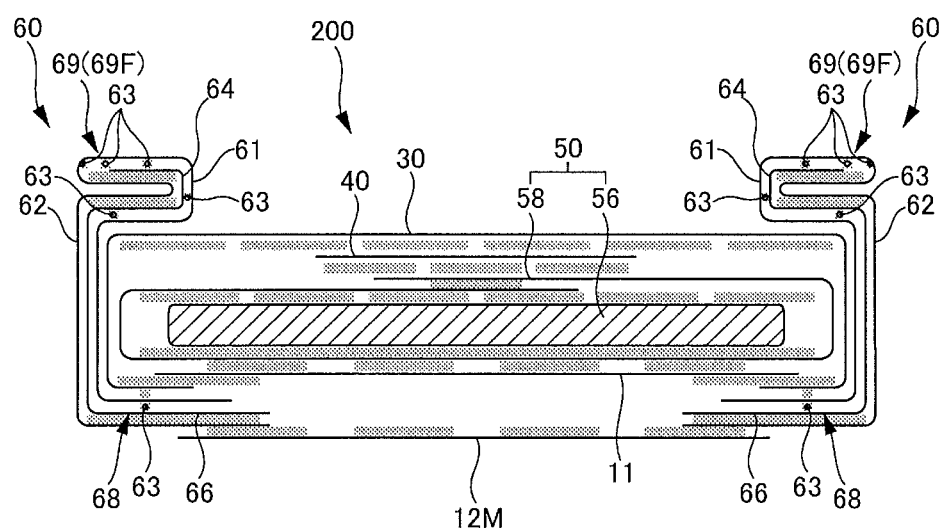
FIG. 7 is a cross-sectional view of an inner member taken along line 3-3 in FIG. 1.
Figure 8:
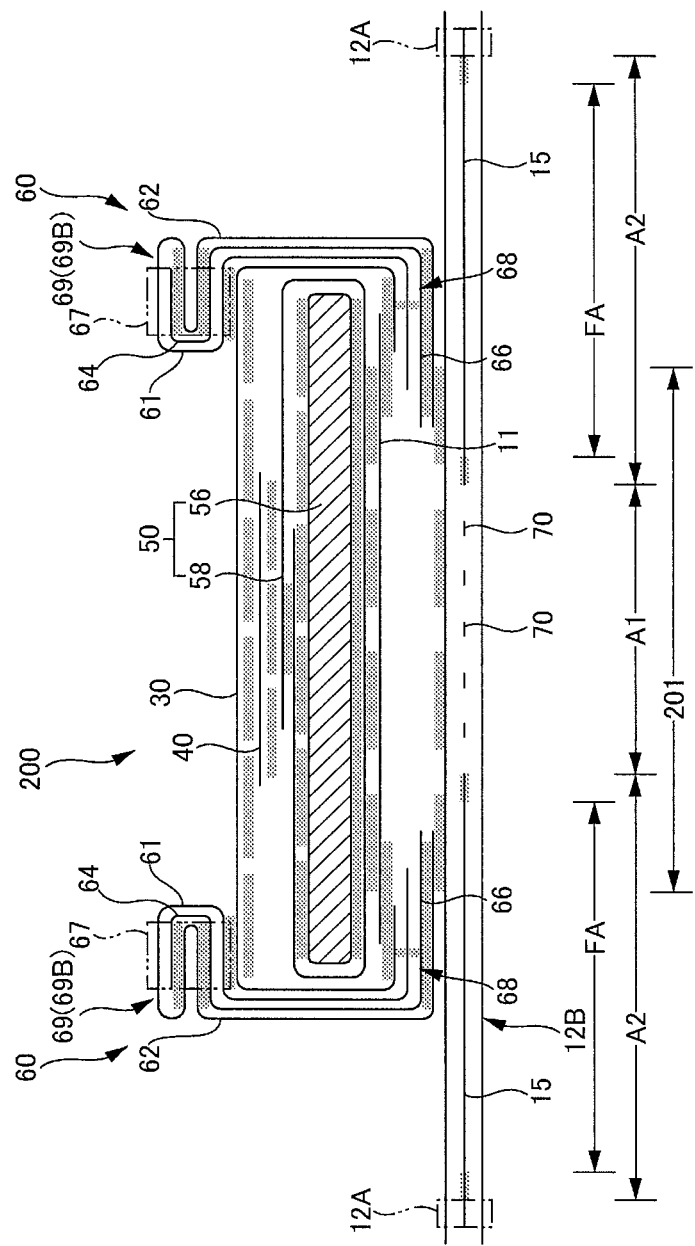
FIG. 8 is a cross-sectional view of the inner member taken along line 4-4 in FIG. 1.

If the two sides of the top sheet 30 in the width direction do not function as the covering material of the liquid impervious sheets 64 of the leg-surrounding gathers 60, the top sheet 30 can be passed between the absorbent element 50 and the leg-surrounding gathers 60 to the back side of the absorbent element 50 and bonded to the liquid impervious sheet 11 and the leg-surrounding gathers 60 with a hot-melt adhesive to prevent permeation of liquid, as illustrated in FIGS. 7 and 8.

(Intermediate Sheet)

With reference to FIGS. 7 and 8, an intermediate sheet (which is also referred to as "second sheet") 40 having hydrophilicity higher than that of the top sheet may be disposed on the back face of the top sheet 30. The intermediate sheet 40 prevents back-flow of liquid absorbed by the absorber and establishes a dry texture of the surface of the top sheet 30. The intermediate sheet 40 may be omitted.

Examples of materials for the intermediate sheet 40 include the same materials for the top sheet 30, spunlace fabric, spunbond fabric, SMS, pulp non-woven fabric, a sheet composed of a mixture of pulp and rayon, pointbond fabric, and crepe paper. Air-through non-woven fabric is particularly preferred for its bulkiness. Air-through non-woven fabric is preferably composed of composite fibers having a core-in-sheath structure. In such a case, the core is composed of a resin, such as polypropylene (PP), preferably polyester (PET) having high stiffness. The basis weight is preferably within the range of 20 to 80 g/m$^2$, more preferably 25 to 60 g/m$^2$. The thickness of the raw fibers of the non-woven fabric is preferably within the range of 2.2 to 10 dtex. For the bulkiness of the non-woven fabric, it is preferred that all or some of the raw fibers be mixed fibers, such as offset-core fibers having an eccentric core, hollow fibers, or hollow off-set core fibers.

The intermediate sheet 40 according to the illustrated embodiments has a width smaller than that of the absorber 56 and is disposed in the central area. Alternatively, the intermediate sheet 40 may be disposed over the entire width. The intermediate sheet 40 may have a longitudinal length the same as that of the absorber 56 or may have a small length centered on the section receiving liquid.

(Liquid Impervious Sheet)

The liquid impervious sheet 11 disposed on the back face of the absorber 56 may be composed of any material. Examples include plastic films composed of olefin resin, such as polyethylene and polypropylene. It is preferred that the liquid impervious sheet 11 be composed of a material having liquid imperviousness and moisture permeability, which is nowadays preferred in view of prevention of stuffiness. An example of a common plastic film having moisture permeability is a microporous plastic film produced through kneading an olefin resin, such as a polyethylene resin or a polypropylene resin, and an inorganic filler, forming a sheet with the kneaded materials, and monoaxially or biaxially stretching the sheet.

The liquid impervious sheet 11 may extend further laterally than the absorber 56 and also function as the liquid impervious sheet 64 in the leg-surrounding gathers 60, as illustrated in FIGS. 3 and 4. Alternatively, the liquid impervious sheet 11 may have a width smaller than that of the back face of the absorbent element 50, as illustrated in FIGS. 7 and 8, or extend along the two sides of the absorbent element 50 in the width direction to reach the edges of the faces of the absorbent element 50 adjacent to the top sheet 30.

The inner face of the liquid impervious sheet 11, in particular the face adjacent to the absorber 56 may be provided with an excretion indicator that changes color in response to absorption of liquid.

(Absorbent Element)

The absorbent element 50 includes an absorber 56 and a package sheet 58 covering the entire absorber 56. The package sheet 58 may be omitted.

(Absorber)

The absorber 56 may be composed of a fiber assembly. Examples of the fiber assembly include fluff pulp, an assembly of short fibers, such as synthetic fibers, assembled through fiber stacking, and an assembly of filaments acquired through opening tows (fiber bundles) of synthetic fibers, such as cellulose acetate, as required. The fiber basis weight of fluff pulp or stacked short fibers may be within the range of approximately 100 to 300 $g/m^2$, and the fiber basis weight of a filament assembly may be within the range of approximately 30 to 120 $g/m^2$, for example. The fineness of synthetic fiber is within the range of 1 to 16 dtex, preferably 1 to 10 dtex, more preferably 1 to 5 dtex. Although the filaments in a filament assembly may be composed of non-crimped fiber, it should preferably be crimped fiber. The degree of crimp of crimped fiber is for example within the range of 5 to 75 per inch, preferably 10 to 50 per inch, more preferably 15 to 50 per inch. Uniformly crimped fiber is often used. It is preferred that high absorbent polymer particles be dispersed in the absorber 56.

The absorber 56 may have a rectangular shape. It is preferred that the absorber 56 be disposed on and between the front end portion and the back end portion and have a shape similar to the outline of an hourglass in which the curved portion has a width smaller than that of the front end portion and the back end portion, as illustrated in FIG. 6, because the fit of the absorber 56 and the leg-surrounding gathers 60 to the legs is enhanced.

The absorber may have any appropriate dimensions. It is preferred that the absorber extends in the front-back and width directions to the peripheral edges of the inner member or the vicinity thereof. Reference sign 56X represents the width of the absorber 56.

(High Absorbent Polymer Particles)

The absorber 56 may partially or entirely contain high absorbent polymer particles. High absorbent polymer particles include "powder" in addition to "particles." The high absorbent particles 54 may be those used for similar types of absorbent articles. Preferred examples of such particles include particles of 30 weight % or less remaining on a standard 500-μm sieve (JIS Z8801-1:2006) after sifting (shook for five minutes) or particles of 60 weight % or more remaining on a standard 180-μm sieve (JIS Z8801-1:2006) after sifting (shook for five minutes).

There is no particular limitation on the material for the superabsorbent polymer particles. Preferably, the material has water absorption capacity (JIS K7223-1996 "Testing method for water absorption capacity of super absorbent polymers") of 40 g/g or more. Examples of the superabsorbent polymer particles are based on starch, cellulose, and synthetic polymer, such as graft copolymer of starch and acrylic acid (salt), saponified copolymers of starch and polyacrylonitrile, cross-linked sodium carboxymethyl cellulose, and acrylic acid (salt) copolymer. Preferably, the superabsorbent polymer particles are in the form of generally used particulate. Alternatively, the high absorbent polymer particles may have another form.

The high absorbent polymer particles have a water absorption rate of 70 second or less, preferably 40 seconds or less. A water absorption rate too small causes ready back-flow of the liquid in the absorber 56 to the outside of the absorber 56.

The basis weight of the superabsorbent polymer particles can be appropriately determined in accordance with the required absorption volume of the absorber 56 depending on use. Although the basis weight depends on the use, it may be within the range of 50 to 350 $g/m^2$. A basis weight of polymers of less than 50 $g/m^2$ fails to achieve a sufficient absorption volume. A basis weight of polymers of more than 350 $g/m^2$ saturates the absorption volume.

The content of the high absorbent polymer particles in the absorber 56 may be variable in the planer direction, as required. For example, the content of the liquid excretion site may be higher than that of other sites. In consideration of the difference between male and female physiology, the content can be increased in the front portion in diapers for male and the content can be increased in the central portion in diapers for female. Alternatively, sections free from polymers may be provided locally (in spots, for example) in the planar direction of the absorber 56.

(Package Sheet)

Examples of the material for the package sheet 58 include liquid pervious materials, such as tissue paper, crepe paper, non-woven fabric, polyethylene laminated non-woven fabric, and a porous sheet. Preferably, the highly absorbent polymer particles do not pass through the sheet. In the case where non-woven fabric is used in place of crepe paper, hydrophilic SMS (SMS or SSMMS) non-woven fabric is preferred. Examples of such materials include polypropylene and polyethylene/polypropylene composite. The basis weight is within the range of 5 to 20 $g/m^2$, preferably 8 to 15 $g/m^2$.

The package sheet 58 may have any appropriate configuration. In view of ready production and prevention of leakage of high absorbent polymer particles from the front-back edges, it is preferred that the package sheet 58 be cylindrically wound around the front and back faces and the two sides of the absorber 56, the front-back edges of the package sheet 58 respectively protrude from the front and back of the absorber 56, and the protrusion be compressed in the front-back direction and bonded with a bonding means, such as a hot-melt adhesive.

(Leg-Surrounding Gathers)

The leg-surrounding gathers 60 extend along the two sides in the width direction of the absorbing face of the inner member 200 and erect toward the legs of the wearer, to prevent side leakage of urine or loose stool due to lateral migration of the urine or loose stool along the top sheet 30.

With reference to FIGS. 3 and 4, the leg-surrounding gathers 60 of this embodiment each includes inner non-woven fabric layers 61 constituting the inner face in the width direction; an outer non-woven fabric layer 62 constituting the outer face in the width direction; elastically stretchable gather materials 63 disposed between the inner non-woven fabric layer 61 and the outer non-woven fabric layer 62 along the front-back direction at at least the distal edge of the intermediate portion in the front-back direction; and a liquid impervious sheet 64 (11) disposed between the inner non-woven fabric layer 61 and the outer non-woven fabric layer 62 across an area between the proximal edge and a position closer to the distal edge than the proximal edge. In this embodiment, fabric-free sections 65 (free from the non-woven fabric) are defined as sections of the leg-surrounding gathers 60 including the liquid impervious sheet 64 in respective areas between the distal edges and the proximal edges, extending entirely over the leg-surrounding gathers 60 in the front-back direction, free from the inner non-woven fabric layers 61, and exposing the liquid impervious sheet 64. The fabric-free sections 65 free from the inner non-woven fabric layers 61 in the leg-surrounding gathers 60 can reduce the volume of non-woven fabric to be used. The distal edges of the leg-surrounding gathers 60 come into contact with the skin of the wearer. The fabric-free sections 65 disposed remote from the distal edges prevent the liquid impervious sheet 64 from coming into contact with the skin of the wearer, thereby preventing deterioration of the texture.

The entire liquid impervious sheet 64 may be covered with the inner non-woven fabric layers 61 extending to the edges of the top sheet 30, as illustrated in FIGS. 1 to 6, or the leg-surrounding gathers 60 having the structure illustrated in FIG. 7 or 8.

The elastically stretchable gather materials 63 may be disposed only at the distal edges of the respective leg-surrounding gathers 60. It is preferred that multiple elastically stretchable gather materials 63 be disposed between the distal edges and the proximal edges of the respective leg-surrounding gathers 60 at predetermined intervals, as illustrated in the drawing. Usually, the number of elastically stretchable gather materials 63 is preferably within the range of 2 to 6, and the intervals 60d thereof are preferably within the range of 3 to 10 mm. The multiple elastically stretchable gather material 63 disposed at the predetermined intervals in this way causes the sections corresponding to the intervals of the elastically stretchable gather material 63 to externally curve. Thus, it is preferred that the fabric-free sections 65 only be provided in these sections, as illustrated in the drawings, because the liquid impervious sheet 64 exposed in the fabric-free sections 65 is depressed and barely comes into contact with the skin of the wearer. In this case, with reference to FIGS. 1 to 6, it is preferred that at least one elastically stretchable gather material 63 be respectively disposed at least only at the distal edge and the proximal edge of each leg-surrounding gather 60 at predetermined intervals, and the fabric-free sections 65 be disposed only in the sections corresponding to the intervals between the elastically stretchable gather material 63 disposed at the proximal edge and the elastically stretchable gather material 63 disposed at the distal edge.

The front-back areas of the leg-surrounding gathers 60 in which the elastically stretchable gather materials 63 are disposed may extend over the entire front-back direction of the leg-surrounding gathers 60. It is preferred that the front-back areas be smaller than front-back areas of the erected areas of the leg-surrounding gathers 60.

The elastically stretchable gather materials 63 may be disposed on either the inner side of the liquid impervious sheet 64 disposed inside the leg-surrounding gathers 60, as illustrated in FIGS. 3 and 7, or the outer side of the liquid impervious sheet 64 (not shown), with proviso that the elastically stretchable gather materials 63 are disposed between the inner non-woven fabric layer 61 and the outer non-woven fabric layer 62 (thus, not disposed in the fabric-free sections 65).

Each edge of the liquid impervious sheet 64 can be disposed anywhere between the proximal and distal edges of the corresponding leg-surrounding gather 60, for example, in an area between the proximal edge and an intermediate position between the proximal and distal edges. It is preferred that each edge of the liquid impervious sheet 64 be aligned with the corresponding distal edge to achieve sufficient imperviousness. In particular, it is preferred that each edge of the liquid impervious sheet 64 be disposed slightly remote from the corresponding distal edge (for example, by several elastically stretchable gather materials, approximately 5 to 30 mm, in specific), as illustrated in FIGS. 3 and 4, so that the liquid impervious sheet 64 does not reach inside of the distal edges to maintain softness.

In the configuration in which the liquid impervious sheet 64 is exposed at the fabric-free sections 65, the liquid impervious sheet 64 exposed at the fabric-free sections 65 may urge against the skin of the wearer in the regions 60W of the leg-surrounding gathers 60 where the front outer member 12F and the back outer member 12B overlap. With reference to FIGS. 1 to 6, the regions 60W can be fixed to the front outer member 12F and the back outer member 12B and be contracted in the width direction by the resilient and elastic members 15 and 19 of the front outer member 12F and the back outer member 12B. In this way, even if the liquid impervious sheet 64 is exposed, the contact area with the skin in the regions 60W is significantly reduced by the contracted wrinkles, thereby reducing the influence on the texture. Sections of the leg-surrounding gathers 60 according to this embodiment disposed between the regions 60W fixed to the front outer member 12F and the back outer member 12B erect toward the legs of the wearer from the proximal edges adjacent to the absorber 56 in response to contraction of the elastically stretchable gather materials 63, as indicated by the dash-double dot lines in FIG. 3.

The leg-surrounding gathers 60 may have any known structure. With reference to FIGS. 1 to 6, the top sheet 30 is composed of non-woven fabric, and the two side edges thereof in the width direction extend across the side edges of the absorber 56; a gather sheet 66 composed of a non-woven fabric is disposed on the back face of the absorber 56, the two side edges thereof in the width direction extending across the side edges of the absorber 56, the side edges of the gather sheet 66 being folded back; the distal edges of the folded portions 66r are remote from the distal edges of the top sheet 30; and the liquid impervious sheet 64 is disposed at least between the two folded portions 66r of the leg-surrounding gathers 60 and between the top sheet 30 and the gather sheet 66. As a result, the portion of the gather sheet 66 other than the folded portions 66r constitute the outer non-woven fabric layer 62; the folded portions 66r of the gather sheet 66 and the portions of the top sheet 30 extending laterally from the absorber 56 constitute the inner non-woven fabric layers 61; and the gaps between the folded portions 66r of the gather sheet 66 and the top sheet 30 constitute the fabric-free sections 65. As described above, portions of the inner non-woven fabric layer 61 closer to the proximal edges of the leg-surrounding gathers 60 relative to the fabric-free sections 65 are formed of the top sheet 30 and the other portions are formed of the gather sheet 66. In this way, the fabric-free sections 65 can be provided without cutting of the material, thereby achieving a significantly simple structure that can be readily produced.

In such a case, it is preferred that the liquid impervious sheet 64 of the leg-surrounding gathers 60 extend from one of the leg-surrounding gathers 60 to the other leg-surrounding gather 60 across the back face of the absorber 56, as illustrated in FIGS. 3 and 4, to achieve uniform imperviousness in not only the leg-surrounding gathers 60 but also on the back face of the absorber 56. Alternatively, the liquid impervious sheet 64 disposed inside the leg-surrounding gathers 60 and the liquid impervious sheet 11 covering the back face of the absorber 56 may be provided separately, as illustrated in FIGS. 7 and 8. In the latter case, the material for the liquid impervious sheet 64 disposed inside the leg-surrounding gathers 60 and the material for the liquid impervious sheet 11 covering the back face of the absorber 56 may either be the same or different.

Similarly, it is preferred that the gather sheet 66 also be composed of a single sheet extending from one of the leg-surrounding gathers 60 to the other leg-surrounding gather 60 across the back face of the absorber 56, as illustrated in FIGS. 3 and 4, because a fabric-like external face can be produced without a separate crotch cover sheet described above. Alternatively, the gather sheet 66 and a crotch cover sheet 12M may be provided separately, as illustrated in FIGS. 7 and 8.

Another structure of the leg-surrounding gathers 60, such as that illustrated in FIGS. 7 and 8, may include attachment portions 68 that are fixed to the back face of the inner member 200; extending portions 69 that extend from the respective attachment portions 68 to the periphery of the front face of the inner member 200 along the sides of the inner member 200; folded portions 69B in which the front-back edges of the respective extending portions 69 are fixed to the periphery of the front face of the inner member 200 in a folded state; free portions 69F in which the intermediate region of the folded portions in the extending portions are unfixed; and elastically stretchable gather materials 63 that are fixed at least along the distal edges of the free portions 69F in the front-back direction in a stretched state. The free portions 69F of the respective leg-surrounding gathers 60 erect toward the respective legs of the wearer from the borders of the respective attachment portions 68 in response to contraction of the elastically stretchable gather materials 63.

The extending portions 69 of the respective leg-surrounding gathers 60 illustrated in FIGS. 7 and 8 have proximal sections adjacent to the center in the width direction and distal sections folded back outward in the width direction from the distal edges of the proximal sections. Alternatively, the extending portions 69 may only have sections that are not folded back outward in the width direction and extend toward the center in the width direction (not shown).

In the front-back intermediate regions of the leg-surrounding gathers 60, which are to be erected, the inner non-woven fabric layer 61 and the outer non-woven fabric layer 62 can be bonded and the elastically stretchable gather materials 63 can be fixed between the fabric layers 61 and 62, with at least one of the hot-melt adhesive through various application methods and a fixing means, such as heat sealing or ultrasonic sealing, through welding of the materials. It is preferred that the portions other than the bonded portions of the elastically stretchable gather materials 63 not be bonded or be weakly bonded because bonding of the entire faces of the inner non-woven fabric layer 61 and the outer non-woven fabric layer 62 impairs softness. In this embodiment, the elastically stretchable gather material 63 are disposed between the inner non-woven fabric layer 61 and the outer non-woven fabric layer 62 after applying a hot-melt adhesive only to the circumferential surfaces of the elastically stretchable gather materials 63 with an application means, such as a comb gun or a Surewrap nozzle. In this way, the elongated resilient and elastic members are fixed to the inner non-woven fabric layer 61 and the outer non-woven fabric layer 62, and the inner non-woven fabric layer 61 is fixed to the outer non-woven fabric layer 62, with only a hot-melt adhesive applied to the circumferential surfaces of the elastically stretchable gather materials 63.

In the front-back unerected regions on the two sides of the leg-surrounding gathers 60 in the front-back direction, the inner non-woven fabric layer 61 and the outer non-woven fabric layer 62 can be bonded together, the leg-surrounding gathers 60 can be fixed to the front outer member 12F and the back outer member 12B, as illustrated in FIGS. 1 to 6, the proximal portions and the distal portions can be fixed in the leg-surrounding gathers 60, as illustrated in FIGS. 7 and 8, and the proximal portions and the distal portions can be fixed to the inner member 200, with at least one of the hot-melt adhesive through various application processes and a fixing means 67, such as heat sealing or ultrasonic sealing, through welding of the materials. In this embodiment, the hot-melt adhesive and the fixing means 67 by welding of the materials are combined. Alternatively, only one of these means may be used for the fixing.

The dimensions of the leg-surrounding gathers 60 can be appropriately selected. For disposable baby diapers, the vertical length of each leg-surrounding gather 60 (the distance between the distal edge and the proximal edge in the width direction in an unfolded state) is in the range of 15 to 60 mm, preferably 20 to 40 mm.

In the embodiments described above, it is preferred that the inner non-woven fabric layer 61 and the outer non-woven fabric layer 62 be composed of soft, uniform non-woven fabric having satisfactory sealing properties, such as spunbond non-woven fabrics (SS, SSS), SMS non-woven fabrics (SMS, SSMMS), and meltblown non-woven fabrics, provided with a water repellent finish of silicone, for example, as required. The fiber basis weight is preferably within the range of approximately 10 to 30 $g/m^2$. With reference to FIGS. 3 and 4, it is apparent from the top sheet 30 constituting the inner non-woven fabric layer 61 closer to the proximal edges than the fabric-free sections 65 that the inner non-woven fabric layer 61 and the outer non-woven fabric layer 62 may each be partially composed of different materials. Alternatively, the inner non-woven fabric layer 61 and the outer non-woven fabric layer 62 may be composed of different materials.

In the embodiments described above, the elastically stretchable gather materials 63 may be resilient and elastic members, such as rubber threads or strips. The thickness of the rubber threads is preferably within the range of 470 to 1240 dtex, more preferably, 620 to 940 dtex. The elongation rate in a fixed state is preferably within the range of 150% to 350%, more preferably, 200% to 300%.

In the embodiments described above, one leg-surrounding gather 60 is disposed on each of the right and left sides. Alternatively, multiple leg-surrounding gathers 60 may be disposed.

<Evaluation Test>

Samples were prepared according to examples 1 and 2 described below, and 30 participants determined the samples having a softer texture in an unstretched state.

EXAMPLE 1

Two spunbond non-woven fabrics composed of polypropylene fiber (fineness 2.2 dtex, basis weight 15 $g/m^2$) having a MD length of 100 mm and a CD length of 100 mm were prepared. A hot-melt adhesive of 10 g/m² in volume was applied on the two MD edges of a first sheet layer; rubber threads stretched at a stretch rate of 270% and having a thickness of 470 dtex were disposed in parallel with each other on the first sheet layer at 5-mm intervals 19d in the CD; a second sheet layer was disposed over the rubber threads with the MD and the CD aligned with those of the first sheet layer; an ultrasonic seal was then applied in a pattern substantially continuous in the MD (the pattern illustrated in FIG. 12) in the areas between adjacent resilient and elastic members; and the two sheet layers were bonded, to prepare a stretchable sheet sample in which the MD is the stretchable direction and the CD is the direction orthogonal to the stretchable direction. The dimensions and intervals of the sheet bonding sections were as follows:

Maximum length 20x of the sheet bonding sections in the stretchable direction: 1.57 mm Maximum length 20y of the sheet bonding sections in the orthogonal direction: 0.70 mm Interval 20t of the sheet bonding sections in the stretchable direction: 1.23 mm (0.78 times the maximum length 20x of the sheet bonding sections in the stretchable direction)

Interval 20d of the sheet bonding sections in the orthogonal-direction: 0.70 mm (1.0 time the maximum length 20y of the sheet bonding sections in the orthogonal direction)

Overlapping width 20w of the sheet bonding sections in the orthogonal-direction: 0.17 mm (0.24 times the orthogonal-direction interval 20d of the sheet bonding sections)

Length 20z of an area of the inter-free region including the sheet bonding sections in the orthogonal-direction: 1.25 mm Interval 20s of the sheet bonding sections in an adjacent inter-free region in the orthogonal-direction: 6.75 mm

EXAMPLE 2

Figure 17:
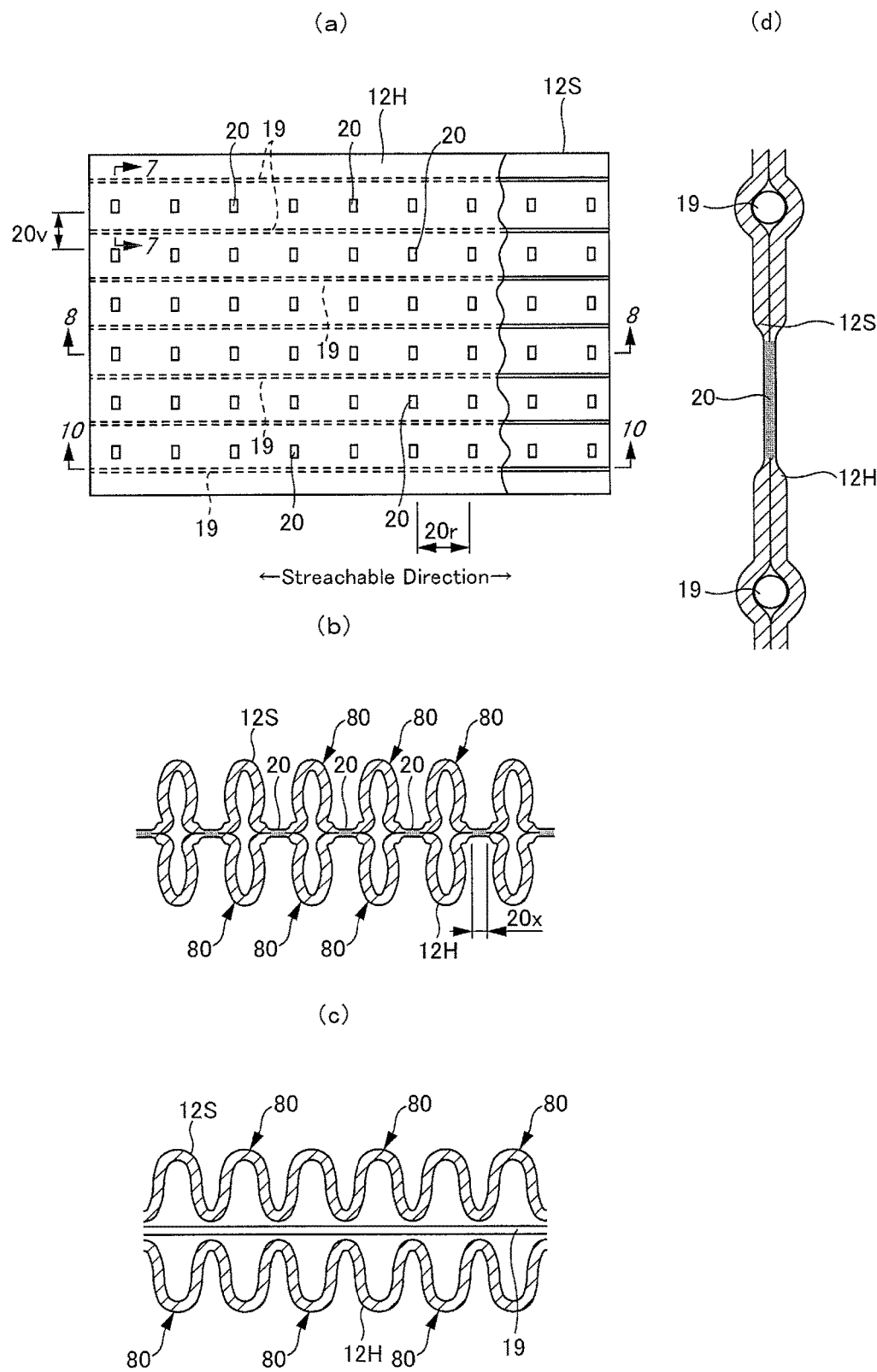
FIG. 17(a) is an enlarged plan view of essential components of the outer member in an unfolded state.
FIG. 17(b) is a cross-sectional view of the outer member taken along line 8-8 in an unstretched state.
FIG. 17(c) is a cross-sectional view of the outer member taken along line 10-10 in an unstretched state.
FIG. 17(d) is a cross-sectional view of the outer member taken along line 7-7 in an unstretched state.
Figure 18:
FIG. 18 is a photograph comparing a sample according to the present invention with the stretchable structures of a commercially available product.
Figure 19:
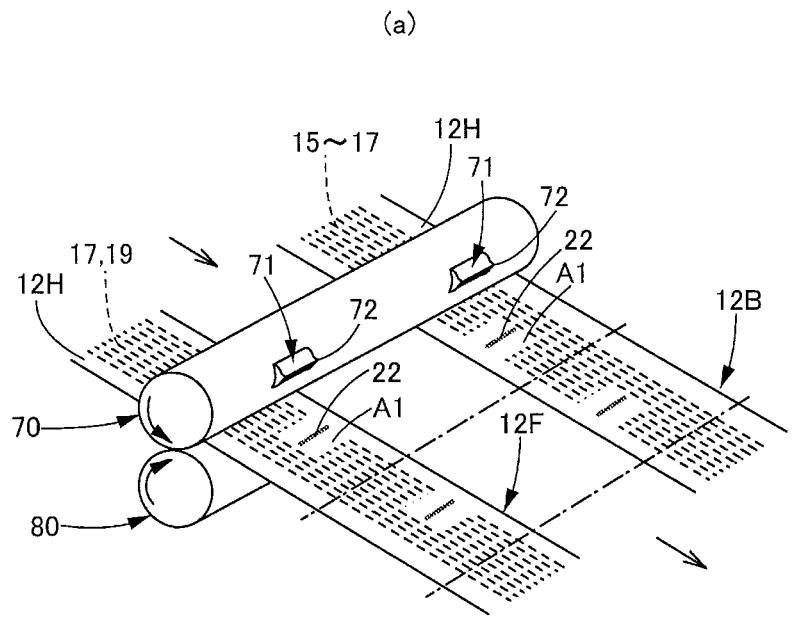
FIG. 19 is a perspective view of a cutter.
Figure 19:
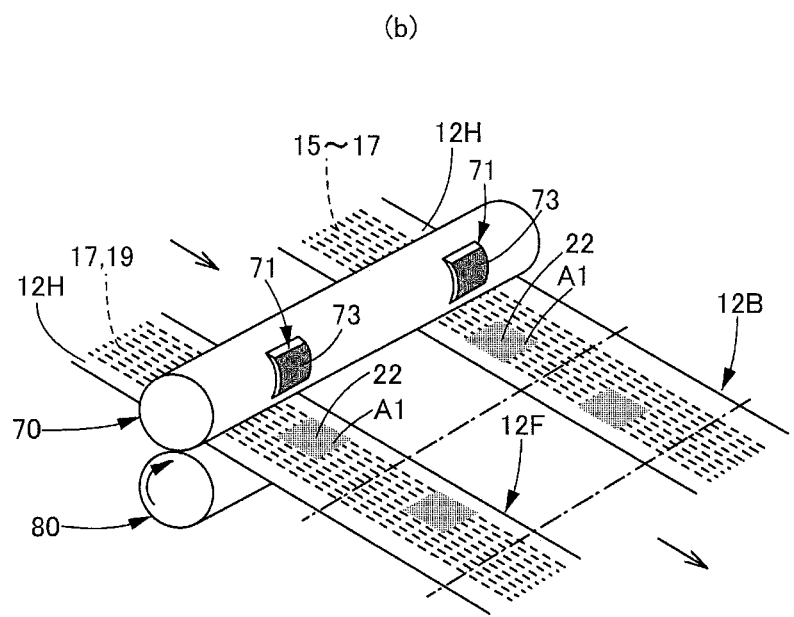

An ultrasonic seal was formed in a pattern illustrated in FIG. 17 as in Example 1 where the dimensions and intervals of the sheet bonding sections 20 were as follows:

Dimensions of each sheet bonding section (length 20x in the stretchable direction×length 20y in the orthogonal direction): 0.8 mm×5.0 mm Intervals 20r of the sheet bonding sections in the stretchable direction: 8.0 mm Intervals 20v of the sheet bonding sections in the orthogonal-direction: 3.0 mm (Results of Evaluation)

All the 30 participants perceived Example 1 to be softer than Example 2.

<Others>

(a) The material for the two sheet layers 12S and 12H can be appropriately selected. It is preferred that the material have a bending resistance in the stretchable direction higher than that in the direction orthogonal to the stretchable direction because the tops of the corrugations 80 can readily and gradually bend.

(b) It is preferred that the sheet bonding sections 20 be disposed in every area between the resilient and elastic members 19 adjacent to each other in the front-back direction, as in the embodiments described above. Alternatively, the sheet bonding sections 20 may be disposed in the areas between every several resilient and elastic members adjacent to each other. In specific, it is preferred that one resilient and elastic member 19 be disposed between every sheet bonding sections 20 adjacent to each other in the front-back direction. Alternatively, several resilient and elastic members 19 may be disposed.

(c) A single sheet bonding section 20 is disposed between two adjacent resilient and elastic members 19 in the front-back direction (the section substantially continuous is defined as one sheet bonding section 20) as in the embodiments described above. Alternatively, multiple sheet bonding sections 20 may be disposed, as illustrated in FIG. 13.

(d) In the embodiments described above, the present invention is applied to the entire stretchable structure in the width direction of the outer members 12F and 12B. Alternatively, the present invention may be applied to a portion of the stretchable structure, and the remaining portion (only the waist region, for example) may have a known stretchable structure in which a hot-melt adhesive is applied to only the circumferential surface of the entire resilient and elastic members 19 along the width direction and the resilient and elastic members 19 are fixed between the two sheet layers 12S and 12H. Alternatively, the present invention may be applied to only one of the front outer member 12F and the back outer member 12B.

(e) The stretchable structure of the present invention described above can be applied not only to underpants-type disposable diapers but also to other stretchable members, such as three-dimensional gathers and flat gathers commonly used in the waist regions and the fastening tapes of tape-type disposable diapers and absorbent articles in general.

<Descriptions of Terms Used in Specification>

The following terms used in the specification should be understood to have the meanings defined below unless otherwise defined in this specification.

"Front-back (longitudinal) direction" refers to the direction connecting the ventral (front) side and the dorsal (back) side, and "width direction" refers to the direction orthogonal to the front-back direction (right-left direction).

"Developed state" refers to a flat unfolded state without contraction or looseness.

"Stretch rate" refers to a value with respect to 100% representing the unstretched state.

"Basis weight" is measured as follows. After preliminary drying of a sample or test piece, the sample or test piece is left in a test room or a test device under normal conditions (an ambient temperature of 20±5° C. and a relative humidity of 65% or less) until the weight of the sample or test piece reaches constant mass. Preliminary drying is to achieve the constant mass of the sample or test piece under an environment having a relative humidity within the range of 10% to 25% and a temperature not exceeding 50° C. For fibers having a standard moisture regain of 0.0%, preliminary drying may be omitted. The test piece having constant mass is cut with a cutting template (200×250 mm, ±2 mm) into samples of 200×250 mm (±2 mm) The weight of the sample is measured. The measured weight is multiplied by 20 to determine the weight per square meter, which is defined as the basis weight.

"Thickness" is automatically measured with an automatic thickness gauge (KES-G5 handy compression tester) under a load of 10 gf/cm² in a pressurized area of 2 cm².

"Water absorption capacity" is measured in accordance with JIS K7223-1996 standard "Testing Method for Water Absorption Capacity of Superabsorbent Polymers."

"Water absorption rate" is defined as "time that elapses before the end point" measured with superabsorbent polymers (2 g) and a normal saline solution (50 g) in accordance with JIS K7224-1996 "Testing Method for Water Absorption Rate of Super Absorbent Polymers."

"Bending resistance" refers to "8.21.1 Method A (45° C.antilever Method)" of JIS L 1096:2010 "Testing Methods for Woven and Knitted Fabrics."

The tests and measurements are carried out in a laboratory or an apparatus under normal conditions (a temperature of 20±5° C. and a relative humidity of 65% or less at the testing site), unless the environmental condition for the tests and measurements are otherwise specified.

The dimensions of the components are measured in an unfolded state, not a unstretched state, unless otherwise specified.

INDUSTRIAL APPLICABILITY

The present invention is suitable for underpants-type disposable diapers such as those described above. Alternatively, the present invention may be applied to absorbent articles in general, such as tape-type or pad-type disposable diapers and sanitary napkins.

REFERENCE SIGNS LIST

11 liquid impervious sheet, 12A side seal portion, 12B back outer member, 12F, 12B outer member, 12F front outer member, 12H inner sheet layer, 12S, 12H two sheet layers, 12S outer sheet layer, 15, 18 under-waist resilient and elastic members, 16 cover resilient and elastic member, 17 waist resilient and elastic member, 19 resilient and elastic member, 19f fixed end, 19m free section, 20 sheet bonding section, 21 unbonded region, 30 top sheet, 40 intermediate sheet, 50 absorbent element, 56 absorber, 58 package sheet, 60 leg-surrounding gather, 61 inner non-woven fabric layer, 62 outer non-woven fabric layer, 63 elastically stretchable gather material, 64 liquid impervious sheet, 65 fabric-free section, 66 gather sheet, 66r folded portion, residual resilient and elastic member, 80 corrugation, 200 inner member, 201 inner-outer fixing portion, A1 non-stretchable region, A2 intermittent stretchable region, A3 continuous stretchable region, FA inter-free region body

The invention claimed is:

1. A stretchable structure of an absorbent article, comprising:
   two sheet layers that extend in a stretchable direction and an orthogonal direction orthogonal to the stretchable direction; and
   a plurality of elongated resilient and elastic members extending in the stretchable direction disposed at intervals in the orthogonal direction between the two sheet layers, wherein,
   each of the resilient and elastic members comprises two fixed ends fixed to the two sheet layers in the stretchable direction, and a free section between the two fixed ends of each of the resilient and elastic members, wherein the free sections of the resilient and elastic members are unfixed to the two sheet layers,
   two adjacent free sections of the resilient and elastic members in the orthogonal direction define an inter-free region including at least one sheet bonding section, the two sheet layers being bonded at the at least one sheet bonding section,
   wherein the two sheet layers are in a contracted state accompanied by contraction of the resilient and elastic members and each of the two sheet layers are configured to conform to each other in a wave pattern, in which one of the two sheet layers follows corrugations formed by an other of the two sheet layers.

2. The stretchable structure of an absorbent article, according to claim 1, wherein,
   the at least one sheet bonding section comprises multiple sheet bonding sections disposed in the inter-free region at intervals in the stretchable direction and the orthogonal direction, and
   the area rate of the sheet bonding sections gradually decreases toward the sides of the inter-free region in the orthogonal direction.

3. The stretchable structure of an absorbent article, according to claim 2, wherein,
   the inter-free region comprises three portions having equal widths in the orthogonal direction in an unfolded state, the three portions comprising a central portion and two side portions positioned on the two sides of the central portion in the orthogonal direction, and
   the area rate of the sheet bonding sections in the side portions is 20% or less of the area rate of the sheet bonding sections in the central portion.

4. The stretchable structure of an absorbent article, according to claim 1, wherein,
   the resilient and elastic members comprise three or more resilient and elastic members disposed at intervals in the orthogonal direction, the resilient and elastic members defining multiple inter-free regions therebetween in the orthogonal direction, and
   the inter-free regions each include the sheet bonding sections intermittently disposed in the stretchable direction, a partial or entire group of the sheet bonding sections disposed in two adjacent inter-free regions in the orthogonal direction is substantially continuous along the stretchable direction.

5. The stretchable structure of an absorbent article, according to claim 1, wherein the two sheet layers have a bending resistance in the stretchable direction higher than the bending resistance in the orthogonal direction.

6. The stretchable structure of an absorbent article, according to claim 1, wherein, in an unfolded state, unbonded regions free from the sheet bonding sections are continuously disposed in the width direction on at least the two sides of the respective inter-free regions in the orthogonal direction, the unbonded regions being disposed over the entire width of the respective inter-free regions.

7. The stretchable structure of an absorbent article, according to claim 6, wherein each of the unbonded regions has a length within a range of 4 to 20 mm in the orthogonal direction.

8. The stretchable structure of an absorbent article, according to claim 1, wherein
   the resilient and elastic members comprises three or more resilient and elastic members disposed at intervals in the orthogonal direction, the resilient and elastic members defining multiple inter-free regions therebetween in the orthogonal direction, and
   the inter-free regions each include the sheet bonding sections.

9. An underpants-type disposable diaper comprising:
   an outer member having the stretchable structure of claim 1 comprising a front body and a back body; and
   an inner member disposed on the inner face of the outer member and comprising an absorber, wherein, side seal portions provided by bonding the two side edges of the outer member of the front body and the respective side edges of the outer member of the back body constitute an annular waist portion, a waist opening, and left and right leg openings, and the stretchable structure is disposed in an area of the outer member including at least two exteriors of the inner member in the width direction, the stretchable direction of the stretchable structure is aligned with the width direction, by which the outer member is configured to be stretchable in the width direction.

10. An underpants-type disposable diaper comprising:
an outer member having the stretchable structure of claim 1 comprising a front body and a back body which are separated or integrated; and
an inner member comprising an absorber, the inner member disposed in a lateral intermediate portion extending from the inner face of the outer member of the front body to the inner face of the outer member of the back body, wherein,
the two side edges of the outer member of the front body is bonded to the respective side edges of the outer member of the back body, to constitute a waist opening and left and right leg openings,
the outer member comprises:
a non-stretchable region that is disposed in a lateral intermediate area and extends in the front-back direction including the absorber; and
intermittent stretchable regions disposed on the two exteriors of the non-stretchable region in the width direction,
the intermittent stretchable regions are disposed such that the stretchable direction of the stretchable structure of an absorbent article according to claim 1 aligns with the width direction, by which the outer member is configured to be stretchable in the width direction,
the non-stretchable region comprises two sheet layers continuing from the intermittent stretchable regions and residual resilient and elastic members, the residual resilient and elastic members comprising at least one of residual pieces remaining between the two sheet layers and continuing from resilient and elastic members in the intermittent stretchable regions and cut pieces of the resilient and elastic members discontinuous from the resilient and elastic members in the intermittent stretchable regions,
the residual resilient and elastic members are unfixed to the two sheet layers, and
in the non-stretchable region, the two sheet layers are bonded at the sheet bonding sections substantially continuous in the width direction on the two sides of the residual resilient and elastic members in the front-back direction.

11. The underpants-type disposable diaper according to claim 10, wherein, the sheet bonding sections in the non-stretchable region are disposed at intervals to define multiple arrays extending in the width direction, the multiple arrays are disposed in the front-back direction, the sheet bonding sections in each first array of the multiple arrays overlap with the sheet bonding sections in the width direction in a second array adjacent to the first array in the front-back direction, and an overlapping width in the width direction of the sheet bonding sections in the first array and the sheet bonding sections in the second array adjacent to the first array in the front-back direction is larger than the interval between the first and second sheet bonding sections in the front-back direction.

12. The underpants-type disposable diaper according to claim 11, wherein, in the non-stretchable region,
the sheet bonding sections have a maximum length within a range of 0.5 to 5.0 mm in the width direction,
the sheet bonding sections in each array have an interval in the width direction of 0.1 to 0.9 times the maximum length of the sheet bonding sections in the width direction, and
the overlapping width in the width direction of the sheet bonding sections in the first array and the sheet bonding sections in the second array in the front-back direction is 0.2 times or more the interval in the front-back direction of the first sheet bonding section and the second sheet bonding section.

13. The underpants-type disposable diaper according to claim 11, wherein, in the non-stretchable region, the sheet bonding sections in the multiple arrays are disposed such that portions of the sheet bonding sections in the front-back direction in the first array overlap with portions of the sheet bonding sections in the front-back direction in the second array in the front-back direction.

14. The underpants-type disposable diaper according to claim 10, wherein
the sheet bonding sections are disposed in a uniform pattern over the entire width of the outer member.

15. The underpants-type disposable diaper according to claim 10, wherein at least the exteriors of the intermittent stretchable regions adjacent to the center in the width direction, the two sheet layers are bonded with a hot-melt adhesive continuously extending over the entire intermittent stretchable regions in the front-back direction, and the hot-melt adhesive constitutes fixed ends of the resilient and elastic members.

16. A stretchable structure of an absorbent article, comprising:
two sheet layers that extend in a stretchable direction and an orthogonal direction orthogonal to the stretchable direction; and
elongated resilient and elastic members extending in the stretchable direction disposed at intervals in the orthogonal direction between the two sheet layers, wherein,
each of the resilient and elastic members comprises two fixed ends fixed to the two sheet layers in the stretchable direction, and a free section between the two fixed ends of each of the resilient and elastic members, wherein the free sections of the resilient and elastic members are unfixed to the two sheet layers,
two adjacent free sections of the resilient and elastic members in the orthogonal direction define an inter-free region including at least one array of sheet bonding sections, the two sheet layers being bonded at the at least one array of sheet bonding sections,
wherein a projection of each sheet bonding section of the at least one array of sheet bonding sections onto the stretchable direction partially overlaps a projection of an adjacent sheet bonding section onto the stretchable direction.

17. The stretchable structure of an absorbent article, according to claim 16, wherein the sheet bonding sections in the inter-free regions are disposed to define multiple arrays extending in the stretchable direction, the multiple arrays are disposed at intervals in the orthogonal direction, sheet bonding sections in each first array of the multiple arrays and sheet bonding sections in a second array adjacent to the first array of the multiple arrays are disposed in a staggered pattern in the orthogonal direction, and an overlapping width in the stretchable direction of the sheet bonding sections in the first and second arrays is larger than an interval between the bonding sections in the first and second arrays in the orthogonal direction.

18. The stretchable structure of an absorbent article, according to claim 17, wherein,
- in the stretchable direction, the sheet bonding sections have a maximum length within a range of 0.5 to 5.0 mm,
- in the stretchable direction, the sheet bonding sections in each array have an interval 0.1 to 0.9 times the maximum length of each of the sheet bonding sections in the stretchable direction, and
- the overlapping width in the stretchable direction of the sheet bonding sections in the first and second arrays of the multiple arrays is 0.2 times or more the interval in the orthogonal direction of the sheet bonding sections in the first and second arrays.

19. The stretchable structure of an absorbent article, according to claim 17, wherein the sheet bonding sections in the multiple arrays are disposed such that portions of the sheet bonding sections in each first array of the multiple arrays in the orthogonal direction overlap with portions of the sheet bonding sections in a second array adjacent to the first array in the orthogonal direction.

\* \* \* \* \*